US006700028B2

(12) United States Patent
Dyroff

(10) Patent No.: US 6,700,028 B2
(45) Date of Patent: Mar. 2, 2004

(54) ADVANCES IN DEHYDROGENATION CATALYSIS

(75) Inventor: David R. Dyroff, St. Louis, MO (US)

(73) Assignee: Huntsman Petrochemical Corporation, Austin, TX (US)

( * ) Notice: Subject to any disclaimer, the term of this patent is extended or adjusted under 35 U.S.C. 154(b) by 64 days.

(21) Appl. No.: 10/140,178

(22) Filed: May 7, 2002

(65) Prior Publication Data

US 2002/0183580 A1 Dec. 5, 2002

Related U.S. Application Data

(62) Division of application No. 09/533,278, filed on Mar. 22, 2000, now Pat. No. 6,417,135.
(60) Provisional application No. 60/151,113, filed on Aug. 27, 1999, provisional application No. 60/155,877, filed on Sep. 24, 1999, and provisional application No. 60/179,984, filed on Feb. 3, 2000.

(51) Int. Cl.$^7$ .............................................. C07C 5/333
(52) U.S. Cl. ..................... 585/660; 585/661; 585/662; 585/663
(58) Field of Search ................................ 585/660, 661, 585/662, 663

(56) References Cited

U.S. PATENT DOCUMENTS

| | | | | |
|---|---|---|---|---|
| 3,201,487 | A | 8/1965 | Kovach et al. | 260/671 |
| 3,234,298 | A | 2/1966 | Van Zijll Langhout et al. | 260/677 |
| 3,274,287 | A | 9/1966 | Moore et al. | 260/683.3 |
| 3,293,319 | A | 12/1966 | Haensel et al. | 260/683.3 |
| 3,315,007 | A | 4/1967 | Abell et al. | 260/683.3 |
| 3,315,008 | A | 4/1967 | Abell et al. | 260/683.3 |
| 3,448,165 | A | 6/1969 | Bloch et al. | 260/683.3 |
| 3,458,592 | A | 7/1969 | Senn, III | 260/683.3 |
| 3,472,763 | A | 10/1969 | Lonyyn et al. | 208/255 |
| 3,484,498 | A | 12/1969 | Berg | 260/671 |
| 3,494,971 | A | 2/1970 | Fenske | 260/671 |
| 3,527,836 | A | 9/1970 | Turner et al. | 260/683.3 |
| 3,576,766 | A | 4/1971 | Rausch | 252/439 |
| 3,585,253 | A | 6/1971 | Huang | 260/683.3 |
| 3,632,662 | A | 1/1972 | Dyroff et al. | 260/683.3 |
| 3,647,719 | A | 3/1972 | Hayes | 252/466 |
| 3,649,566 | A | 3/1972 | Hayes et al. | 252/470 |
| 3,655,621 | A | 4/1972 | Kasperik et al. | 260/677 |
| 3,662,015 | A | 5/1972 | Komatsu et al. | 260/677 |
| 3,662,018 | A | 5/1972 | Parker et al. | 260/683.3 |
| 3,696,160 | A | 10/1972 | Chomyn | 260/677 |
| 3,745,112 | A | 7/1973 | Rausch | 208/139 |
| 3,751,506 | A | 8/1973 | Burress | 260/671 |
| 3,761,531 | A | 9/1973 | Bloch | 260/668 |
| 3,767,594 | A | 10/1973 | Vesely et al. | 252/439 |
| 3,825,612 | A | 7/1974 | Wilhelm | 260/668 |
| 3,887,455 | A | 6/1975 | Hamner et al. | 208/112 |
| 3,920,615 | A | 11/1975 | Huang | 260/683.3 |
| 3,993,601 | A | 11/1976 | Long et al. | 252/462 |
| 3,998,900 | A | 12/1976 | Wilhelm | 260/668 D |
| 4,016,106 | A | 4/1977 | Sawyer et al. | 252/455 R |
| 4,048,246 | A | 9/1977 | Antos | 260/668 D |
| 4,070,413 | A | 1/1978 | Imai | 260/683.3 |
| 4,125,565 | A | 11/1978 | Antos | 260/668 D |
| 4,136,127 | A | 1/1979 | Antos | 260/668 D |
| 4,172,853 | A | 10/1979 | Antos | 585/379 |
| 4,177,218 | A | 12/1979 | Antos | 585/379 |
| 4,207,425 | A | 6/1980 | Antos | 585/434 |
| 4,216,346 | A | 8/1980 | Antos | 585/379 |
| 4,227,026 | A | 10/1980 | Flagg et al. | 585/434 |
| 4,268,706 | A | 5/1981 | Antos | 585/430 |
| 4,278,566 | A | 7/1981 | Hensley, Jr. et al. | 252/465 |
| 4,312,792 | A | 1/1982 | Antos | 252/466 |
| 4,341,664 | A | 7/1982 | Antos | 252/466 |
| 4,343,724 | A | 8/1982 | Antos | 252/466 B |
| 4,358,628 | A | 11/1982 | Slaugh | 585/455 |
| 4,387,259 | A | 6/1983 | Barile | 585/467 |
| 4,396,540 | A | 8/1983 | Antos | 252/466 PT |
| 4,409,401 | A | 10/1983 | Murtha | 568/362 |
| 4,409,410 | A | 10/1983 | Cosyns et al. | 585/259 |
| 4,409,412 | A | 10/1983 | Haag et al. | 585/454 |
| 4,430,517 | A | 2/1984 | Imai et al. | 585/660 |
| 4,486,547 | A | 12/1984 | Imai et al. | 502/223 |
| 4,489,213 | A | 12/1984 | Kovach | 585/467 |
| 4,523,048 | A | 6/1985 | Vora | 585/323 |
| 4,551,574 | A | 11/1985 | Imai et al. | 585/660 |
| 4,595,673 | A | 6/1986 | Imai et al. | 502/227 |
| 4,598,060 | A | 7/1986 | Schoenthal et al. | 502/263 |
| 4,608,360 | A | 8/1986 | Abrevaya et al. | 502/226 |
| 4,677,237 | A | 6/1987 | Imai et al. | 585/444 |
| 4,827,072 | A | 5/1989 | Imai et al. | 585/443 |
| 5,324,880 | A | 6/1994 | Dyroff | 585/660 |
| 5,545,602 | A | 8/1996 | Nelsn et al. | 502/314 |
| 5,677,260 | A | 10/1997 | Dongara et al. | 502/339 |
| 5,827,421 | A | 10/1998 | Sherwood, Jr. | 208/112 |
| 6,191,065 | B1 | 2/2001 | Williams et al. | 502/300 |
| 6,417,135 | B1 * | 7/2002 | Dyroff | 502/325 |

* cited by examiner

Primary Examiner—Thuan D. Dang
(74) Attorney, Agent, or Firm—Christopher J. Whewell

(57) ABSTRACT

Provided herein are processes for the dehydrogenation of hydrocarbons using new supported catalysts. A process according to the invention employs new catalysts that possess a unique pore size distribution which provides a favorable balance of selectivity, activity, and thermal stability. A process according to the invention includes regeneration of the new catalysts. Detergent range paraffins may be converted to monoolefins using the new catalysts with fewer unwanted by-products being formed during the dehydrogenation.

140 Claims, No Drawings

ADVANCES IN DEHYDROGENATION CATALYSIS

This Application is a divisional application of U.S. patent application Ser. No. 09/533,278 filed Mar. 22, 2000, now U.S. Pat. No. 6,417,135 currently still pending, and claims the benefit of U.S. Provisional Application No. 60/151,113 filed Aug. 27, 1999, U.S. Provisional Application No. 60/155,877 filed Sep. 24, 1999, and U.S. Provisional Application No. 60/179,984 filed Feb. 3, 2000 all of which are herein incorporated by reference.

FIELD OF THE INVENTION

The present invention relates to catalysts useful in the dehydrogenation of paraffins, and to methods for using the catalysts. The catalysts of the invention provide a combination of selectivity, thermal stability, and initial catalyst bed activity per unit volume that is highly advantageous. In one preferred embodiment, the invention relates to the dehydrogenation of substantially linear paraffins having between about 9 and 15 carbon atoms per molecule, and monoolefins derived from such paraffins find particular use in the production of biodegradable detergents. Through the use of the catalysts and methods of the invention, it is possible to obtain excellent reaction selectivity in a process that includes regeneration of the catalyst.

BACKGROUND INFORMATION

Many chemical processes that are practiced on a commercial scale involve the use of one or more catalysts for the production of intermediate or finished products. This is particularly the case in the petroleum-dependent arts. Because of the large volumes commonly processed, it is often possible for even incremental improvements in the performance of catalytic processes to provide commercially significant benefits. Examples of important catalytic hydrocarbon conversion processes include alkylation processes, hydrogenation processes, dehydrogenation processes, and isomerization processes.

Although catalysts by definition are not directly consumed by the chemical reactions that they promote, in the aforesaid and other processes catalysts are frequently rendered progressively less active during their use by one or more mechanisms known to those skilled in the art. In some cases, it is possible by taking certain steps such as coke removal, acid washing, or calcining to restore much of the lost activity so that the useful life of the catalyst is extended. Such steps are often referred to as "regeneration" of the catalyst. In general terms, it is highly desirable to employ catalysts that respond well to regeneration, in order to reduce the costs associated with catalyst replacement. However, in many processes catalyst regeneration is not a viable option. For example, a catalyst that might otherwise be regenerable by burning off accumulated coke might not have sufficiently high thermal stability to adequately withstand the high local temperatures that are generated under effective coke burning conditions.

The present invention is concerned with catalytic materials useful in the dehydrogenation of paraffins (saturated hydrocarbons). Dehydrogenation of paraffins is often carried out with the goal of introducing one or more olefinic linkages, either to produce an olefin product useful in and of itself, or to provide an effective "handle" on a molecule for subsequent reaction with some other species. The present invention is particularly concerned with the heterogeneously catalyzed dehydrogenation of detergent range paraffins (paraffins with carbon numbers in the 9–15 range) to obtain products that contain a single unsaturated linkage per molecule (monoolefins). The resulting monoolefins (detergent range monoolefins) are useful for reaction with a second organic species that includes an aromatic nucleus to produce alkylbenzenes. Such alkylbenzenes having substantially linear alkyl substituents attached to benzene rings are useful for conversion to alkylbenzene sulfonates that are employed in detergent formulations in both the industrial and consumer products markets. Alkylbenzenes derived primarily from linear paraffins are particularly advantageous in the production of detergents, since their sulfonates possess a very high degree of biodegradability. The term "substantially linear" as used herein means that the type and degree of branching present in the paraffin that is to be dehydrogenated to obtain olefins for subsequent use in alkylbenzene sulfonate production are limited to those which provide an alkylbenzene sulfonate with a degree of biodegradability that is acceptable according to current standards promulgated by industry and regulatory agencies. Alkylbenzenes containing a single alkyl substituent attached to a benzene ring (monoalkylbenzenes) are advantageous, as is known in the art, since they tend to provide favorable detergent performance characteristics. Alkylbenzene mixtures consisting primarily of monoalkylbenzenes with linear alkyl substituents are also recognized as advantageous, and they are the types most widely used by the detergent industry. Such mixtures are commonly referred to as "linear alkylbenzene" or "LAB" by those skilled in the art.

Production of monoolefins in a dehydrogenation process typically involves the contacting of saturated hydrocarbons with a suitable catalyst under reaction conditions adjusted to favor monoolefin formation. However, the production of monoolefin is inevitably accompanied by some formation of undesirable by-products such as diolefins, aromatics, and cracking products. The amount of diolefin formed depends mainly upon the paraffin structure and the conversion level, and relatively little control of diolefin formation is possible by means of the other reaction conditions. The formation of cracking products can be minimized by using a nonacidic catalyst and by avoiding extremely high temperatures. Aromatics formation is significantly influenced by both the selectivity of the catalyst and the reaction conditions employed. It is well known in the art that great economic advantages can be realized by using a highly selective dehydrogenation catalyst that minimizes the formation of aromatics at a given level of paraffin conversion. Specific advantages associated with lower aromatics formation include lower paraffin consumption, lower consumption of monoolefin by side reactions with aromatics during alkylbenzene production, higher recycle paraffin purity, and less extensive catalyst inhibition and fouling.

Many catalysts useful for the dehydrogenation of paraffins to olefins are known in the art. Typically, known catalyst materials comprise one or more active metals or metal oxides in a finely divided form, deposited upon the surface of particles of a relatively inert carrier substance such as a silica or an alumina. Alternative means known in the art by which the primary catalytic component(s) or precursors thereof may be rendered into the required finely divided state upon the surface of a suitably pretreated support include such methods as precipitation, adsorption from an aqueous solution, and ion exchange techniques that make use of Zeolite® (molecular sieve) carrier materials. Typically, following the deposition of one or more species onto a selected support to provide a raw catalyst, the raw catalyst material is subjected to some sort of heat treatment at an elevated temperature for a suitable time, often in the presence of a controlled atmosphere, which may be inert, oxidizing, or reducing. The prior art is replete with examples of aluminas and silicas of various particle sizes, crystalline phases, pore structures, etc., combined with a very broad variety of other components deposited upon their surfaces. In many cases, the deposited components comprise at least one primary catalytic component and at least one additional component such as an activator, attenuator, or modifier.

In general terms, the performance of a catalyst is largely determined by three critical properties that are readily observable and known to those skilled in the art of catalysis. These properties are 1) selectivity, 2) activity, and 3) thermal stability.

In the case of paraffin dehydrogenation to produce monoolefin, the selectivity of a catalyst is a measure of its ability under appropriate reaction conditions to maximize the fraction of the total converted paraffin that is converted to monoolefin. Since higher formation of each unwanted by-product necessarily results in lower formation of monoolefin at a given paraffin conversion, selectivity is improved if by-product formation is reduced at a given paraffin conversion. Thus, comparisons of catalyst selectivity can be made in terms of the amounts of by-products formed at equal paraffin conversion in runs that use different catalysts but are essentially equivalent in terms of the other reaction conditions. If different low acidity catalysts are being compared, the most important difference will typically be between the amounts of aromatics formed at a given paraffin conversion. In comparing selectivities within a series of alternative catalysts, it is particularly convenient to express the selectivities in comparison to a single standard catalyst. Thus, for each alternative catalyst that exhibits a selectivity improvement, the size of the improvement can be expressed as the percentage by which the alternative catalyst reduces the formation of aromatics at a given paraffin conversion under standard reaction conditions in comparison to the standard catalyst.

In the case of paraffin dehydrogenation, the activity of a catalyst is a measure of its ability to promote paraffin conversion. In a continuous process under any particular reaction conditions, higher catalyst activity results in higher conversion over a given amount of catalyst. For practical purposes, the most important measure of catalytic activity is the volumetric activity, meaning the activity per unit volume of catalyst bed. Under given continuous reaction conditions, a catalyst with higher volumetric activity is able to provide higher paraffin conversion over a catalyst bed of a given volume. Alternatively, it is able to reduce the catalyst bed volume (reactor size) required to produce a given paraffin conversion. Factors which significantly affect the volumetric activity of a catalyst include the surface area, the bulk density, the types and weight percentages of the included active metals, the distributions of the active metals within the support pellets, and the degree of diffusion resistance associated with the pore structure. Since dehydrogenation catalysts lose activity during normal use, comparisons of the activity of different catalyst types must be made at comparable degrees of catalyst deactivation. This can be done by comparing paraffin conversion ranges for runs of equal length that begin with fresh catalyst and employ standard reaction conditions.

A dehydrogenation catalyst must have a high degree of thermal stability in order to hold up adequately under the elevated temperatures encountered during its normal use. High thermal stability is particularly important if the catalyst will be regenerated by burning off accumulated coke, a procedure that tends to produce unusually high local temperatures. A deficiency of thermal stability results in an excessive loss of activity during exposure of the catalyst to high temperatures. One process that contributes to activity loss during thermal exposure involves the agglomeration (coalescence) of particles of the active component(s). Another process involved is degradation of the support structure in such a way that some catalytic particles become entrapped in inaccessible locations within surrounding layers of support material. In either case, the amount of catalytic surface available to the reaction is reduced. The thermal stability of a particular catalyst can be determined by comparing the activities of representative samples from the same lot that have and have not been exposed to a suitable high temperature aging treatment.

It is known that in the catalytic dehydrogenation of detergent range paraffins the percentage conversion to monoolefins in a single pass through the reactor is subject to an equilibrium constraint. While the limiting conversion can vary considerably under various reaction conditions, the actual percentage of monoolefin in the products is typically not greater than about twenty weight percent. It is also well known that the formation of monoolefin in such processes is accompanied by the formation of various less desirable by-products including diolefins, aromatics, and hydrocarbons with carbon numbers below the detergent range which are formed by cracking reactions. As used herein, the term "conversion" means the weight percentage of the detergent range paraffin in the feed that is converted in a single pass to species other than paraffins within the same carbon number range. In cases in which the feed contains species other than detergent range paraffins, these components of the feed are ignored in the calculation of conversion and selectivity. In general, higher conversion and higher selectivity are advantageous, but an increase in conversion tends to lower selectivity.

A well known problem encountered in the production of detergent range olefins by catalytic dehydrogenation of paraffins is the loss of catalyst activity during paraffin processing. The catalyst can lose activity as a result of strong catalyst poisons such as sulfur compounds in the feed, and such activity loss is generally controlled by controlling feed purity. However, even when the feed contains extremely low levels of such poisons, the catalyst tends to deactivate at a significant rate due to the formation of coke on the catalytic surfaces. The rate of coke formation can vary widely depending upon the combination of reaction conditions selected. In general, a lower rate of coke formation is advantageous since this reduces various costs associated with catalyst regeneration or replacement and facilitates the maintenance of both conversion and other reaction conditions within optimum ranges for extended periods of operation.

One method used in prior art paraffin dehydrogenation processes to reduce catalyst deactivation is to mix varying amounts of hydrogen with the vaporized paraffin feed prior to its introduction into the catalytic reaction zone. It is taught in U.S. Pat. No. 4,343,724 for example that such hydrogen serves a "dual-function" in both diluting the paraffin and "suppressing the formation of hydrogen-deficient, carbonaceous deposits" upon the catalyst. In many cases, the amount of added hydrogen used in patent examples has been extremely large, for example 4–8 moles of hydrogen per mole of hydrocarbon. Severe disadvantages accompany such large additions of hydrogen, including an adverse effect upon the equilibrium for monoolefin formation, increased size of most portions of the processing equipment for a given production rate, and increased energy and maintenance costs associated with the recovery, compression, and recycle of hydrogen. Thus, it is greatly advantageous to reduce the hydrogen to hydrocarbon mole ratio ($H_2$:HC ratio) used in the process. U.S. Pat. No. 5,324,880 teaches the use of $H_2$:HC ratios within the range 0.5–1.9, and even lower ratios such as those within the range 0.3–0.5 are useful under some circumstances. However, it appears that some added hydrogen is always necessary in order to maintain the catalyst in an active state.

Typically, the activity of a paraffin dehydrogenation catalyst declines during use until the remaining activity is insufficient to support further economical operation without prior replacement or regeneration of the catalyst. Since the cost of a fresh catalyst charge for an industrially sized reactor system can easily reach into the hundreds of thousands of dollars, it is most desirable to extend the useful life of a given bed of catalyst by regenerating it one or more times prior to its eventual replacement. Costs reduced by catalyst regeneration include those for acquisition of new catalyst, down time and labor associated with catalyst replacement, processing of spent catalyst for precious metal recovery, and replacement of precious metals lost during spent catalyst processing. Furthermore, the necessity of the use of costly equipment for catalyst addition without shutdown of a reactor can be avoided, and occasional episodes of catalyst poisoning are less costly since regeneration of the catalyst is often sufficient to restore normal operation.

The ability of a catalyst to be effectively regenerated is commonly referred to as the regenerability of the catalyst. In order to be regenerable, a catalyst must have a high degree of thermal stability so that activity losses by thermal degradation are minimized during high temperature regeneration procedures such as the burning of accumulated coke. Since some loss of activity during each regeneration is inevitable, another requirement for regenerability is a sufficient amount of activity in the fresh catalyst to compensate for the activity losses incurred during regenerations. A catalyst that is highly regenerable is able to retain an adequate level of activity throughout a series of many operating cycles and intervening regenerations. No laboratory test can completely quantify the degree of regenerability of a catalyst. However, a useful indication of regenerability can be obtained in the laboratory by measuring the initial activity and the thermal stability at a temperature representative of the intended regeneration procedure.

In a process for the production of monoolefins by dehydrogenation of detergent range paraffins, great economic advantages can be realized through the use of a catalyst that has favorable characteristics with regard to selectivity, volumetric activity, thermal stability, and regenerability. In practice, however, previously known catalysts have been deficient in at least one of these properties. Catalysts that have been regenerable have been deficient in selectivity, and catalysts with relatively high selectivity have been deficient in volumetric activity, thermal stability, or regenerability. Thus, the discovery of a catalyst with favorable characteristics with regard to all four of these properties as described herein represents a major advance in the dehydrogenation of paraffins and in the manufacture of alkylbenzene for use in the detergent industry.

The prior art associated with catalytic reactions involving hydrocarbons includes U.S. Pat. Nos. 3,484,498; 3,494,971; 3,696,160; 3,655,621; 3,234,298; 3,472,763; 3,662,015; 4,409,401; 4,409,410; 4,523,048; 3,201,487; 4,358,628; 4,489,213; 3,751,506; 4,387,259; and 4,409,412, the entire contents of which are herein incorporated by reference thereto. Prior art patents directed at catalysts useful for dehydrogenation of hydrocarbons include U.S. Pat. Nos. 3,274,287; 3,315,007; 3,315,008; 3,745,112; and 4,430,517, the entire contents of which are herein incorporated by reference thereto.

The prior art associated with the dehydrogenation of detergent range paraffins to form monoolefins includes U.S. Pat. No. 3,761,531, the entire contents of which are incorporated herein by reference. In this patent is described a dehydrogenation method comprising contacting a hydrocarbon at dehydrogenation conditions with a catalytic composite comprising a combination of catalytically effective amounts of a platinum group component, a Group IV-A metallic component, a Group V-A metallic component, and an alkali or alkaline earth metallic component with an alumina carrier material. It is taught therein that the preferred alumina carrier material has a relatively low apparent bulk density, with a bulk density in the range of about 0.3 to about 0.4 $g/cm^3$ being especially preferred, and a bulk density of about 0.33 $g/cm^3$ to be used for best results. While the catalysts described in U.S. Pat. No. 3,761,531 exhibit an acceptable level of selectivity towards the desired reaction, they generally display relatively poor volumetric activity and/or thermal stability. Consequently, such catalysts are not considered to be regenerable. In typical practice, after a single reaction cycle, a bed of such catalyst is replaced with fresh catalyst. Such recharging is expensive both from the perspective of the cost of the catalyst and in terms of the reactor down time experienced.

Other patents which relate to catalysts and processes useful in the dehydrogenation of detergent range paraffins to form monoolefins are U.S. Pat. Nos. 3,585,253; 3,632,662; 3,920,615; and 5,324,880, the entire contents of which are herein incorporated by reference thereto. The catalysts described in U.S. Pat. No. 3,920,615 have acceptable selectivity, but they were found to be deficient in volumetric activity and/or regenerability. The catalysts described in the other three patents mentioned above rank highly in terms of volumetric activity and regenerability, but they are lacking in that their selectivity is undesirably low.

The following U.S. Patents, the entire contents of each of which are herein incorporated by reference, are useful in illustrating the differences between the prior art and the instant invention: U.S. Pat. Nos. 3,293,319; 3,448,165 (especially col. 5, lines 26–33); U.S. Pat. No. 3,576,766 (esp. col. 5, lines 31–60); U.S. Pat. No. 3,647,719 (esp. col. 4, line 68-col. 5, line 4); U.S. Pat. No. 3,649,566 (esp. col. 5, lines 13–24); U.S. Pat. No. 3,761,531 (esp. col. 4, line 68-col. 5, line 17); U.S. Pat. No. 3,767,594 (esp. col. 2, lines 46–60 and Example I); U.S. Pat. No. 3,825,612 (esp. col. 5, lines 26–38); U.S. Pat. No. 3,998,900 (esp. col. 5, line 60-col. 6, line 3); U.S. Pat. No. 4,048,245 (esp. col. 6, lines 39–51); U.S. Pat. No. 4,070,413 (esp. Example I); U.S. Pat. No. 4,125,565 (esp. col. 6, lines 38–51); U.S. Pat. No. 4,136,127 (esp. col. 6, lines 41–54); U.S. Pat. No. 4,172,853 (esp. col. 6, line 61-col. 7, line 6); U.S. Pat. No. 4,177,218 (esp. Example I and col. 3, line 56-col. 4, line 14); U.S. Pat. No. 4,207,425 (esp. col. 6, lines 33–54); U.S. Pat. No. 4,216,346 (esp. col. 6, lines 40–54); U.S. Pat. No. 4,227,026 (esp. col. 6, lines 36–50); U.S. Pat. No. 4,268,706 (esp. col. 6, lines 38–52; col. 7, line 27-col. 8 line 59; and col. 19, lines 3–10); U.S. Pat. No. 4,312,792 (esp. col. 6, line 63-col. 7, line 9; col. 7, line 54-col. 9, line 19; and col. 19, lines 22–28); U.S. Pat. No. 4,341,664 (esp. col. 6, line 62-col. 7, line 8; col. 7, line 53-col. 9, line 18; and col. 19, lines 1–8); U.S. Pat. No. 4,343,724 (esp. col. 6, line 61-col. 7, line 7; col. 7, line 52-col. 9, line 17; and col. 19, lines 14–21); U.S.

Pat. No. 4,396,540 (esp. col. 6, line 61-col. 7, line 7; col. 7, line 52-col. 9, line 17; and col. 19, lines 5–11); U.S. Pat. No. 4,486,547 (esp. col. 6, line 56-col. 7, line 23); U.S. Pat. No. 4,551,574 (esp. col. 6, line 60-col. 7, line 25); U.S. Pat. No. 4,595,673 (esp. col. 6, lines 15–43); U.S. Pat. No. 4,608,360; 4,677,237 (esp. col. 6, lines 25–33); and U.S. Pat. No. 4,827,072 (esp. col. 10, line 31-col. 11, line 11). These patents are believed to be assigned to UOP, LLC. With the exception of U.S. Pat. No. 4,070,413, these prior art patents have claims limited to the inclusion of one or more elements other than platinum group metals, Group I-B metals, and alkali metals. The remaining patent U.S. Pat. No. 4,070,413 has claims limited to the use of a particular steam-treated alumina support. In each of these patents, the teaching concerning the shape and size of the catalyst particles is that $\frac{1}{16}$ inch spheres are preferred. A few of these patents (U.S. Pat. Nos. 4,268,706; 4,312,792; 4,341,664; 4,343,724; and 4,396,540) teach that $\frac{1}{16}$ inch extrudates are also preferred. All examples used $\frac{1}{16}$ inch spheres, and there is no indication in these patents that extrudates are ever preferred over spheres. Only one of the patents, U.S. Pat. No. 4,608,360, discusses pore size distribution, and it teaches that more than 55% of the total pore volume should be contained in pores with diameters of 600 Angstroms or larger. Higher selectivity was attributed to such a pore structure in Example III of that patent. The teaching concerning average pore size is inconsistent and not very specific. The ranges mentioned for average pore diameter include 20–30, 20–300, and 20–3000 Angstroms. The most preferred bulk densities for spheres were below 0.5 g/cm$^3$ in some of the earlier-issued of these patents, and near 0.3 g/cm$^3$ in all of the remaining patents. Bulk density ranges indicated for extrudates were 0.4–0.85 or 0.5–0.85 g/cm$^3$.

The following U.S. Patents, the entire contents of each of which are herein incorporated by reference, are also useful in illustrating the differences between the prior art and the instant invention: U.S. Pat. No. 5,677,260 (esp. col. 4, lines 50–59); U.S. Pat. Nos. 3,458,592; 3,662,018; 3,527,836; 3,274,287 (esp. col. 3, line 66-col. 4, line 20 and Example IV); U.S. Pat. No. 3,315,007 (esp. col. 3, lines 25–56 and Example I); U.S. Pat. No. 3,315,008 (esp. col. 3, lines 12–44); U.S. Pat. Nos. 3,585,253; 3,632,662 (esp. col. 2, lines 50–61 and col. 3, lines 26–31); U.S. Pat. No. 3,920, 615; and U.S. Pat. No. 5,324,880. The catalysts disclosed in U.S. Pat. No. 5,677,260 believed to be assigned to Indian Petrochemicals include an unusually large number of added elements, and they closely resemble various catalysts disclosed in patents believed to be assigned to UOP, LLC. A preference for $\frac{1}{16}$ inch spheres with bulk density near 0.3 g/cm$^3$ is indicated therein. The preferred pore distribution is said to be "mesoporous"; however, no further definition is included. U.S. Pat. Nos. 3,458,592; 3,662,018; and 3,527, 836 believed to be assigned to Texaco and British Petroleum claim catalysts with molecular sieve supports.

Among the listed patents originally assigned to Monsanto Company, the earliest ones: U.S. Pat. Nos. 3,274,287; 3,315, 007; and 3,315,008 do not mention the use of copper in combination with platinum and a support, while the later ones: U.S. Pat. Nos. 3,585,253; 3,632,662; 3,920,615; and 5,324,880 disclose such. These patents teach that the macropore volume (the volume contained in pores with average diameters above 700 Angstroms) should be at least 0.05 cm$^3$/g and that higher macropore volumes are preferred. They say nothing about bulk density. In U.S. Pat. No. 3,920,615, it is taught that selectivity is improved by calcining to a surface area of less than 150 m$^2$/g. Although such calcination affects the pore structure, no particular final pore structure is defined simply by specifying the surface area. The allowed variations in starting materials and order of operations significantly affect the relationship between surface area and pore structure.

SUMMARY OF THE INVENTION

Although the prior art patents set forth and described above in the Background Information section herein contain a wealth of information concerning the composition and use of various catalysts useful in the dehydrogenation of paraffins, there is nothing in the prior art that points to the conclusion or even suggests that a high degree of volumetric activity, thermal stability, and selectivity heretofore unseen would be provided by a catalyst according to this invention which comprises one or more of the elements: platinum, rhodium, iridium, palladium, ruthenium, and osmium (the "platinum group elements") deposited upon a porous alumina support selected to provide in the finished catalyst a surface area greater than 100 m$^2$/g, a volume of pores with diameters below 60 Angstrom units that is less than 0.05 cm$^3$/g, a volume of pores with diameters in the range of 60–350 Angstrom units that is greater than 0.50 cm$^3$/g, and a volume of pores with diameters in the range of 60–350 Angstrom units that is greater than 70% of the total contained pore volume. In a preferred form of the invention, the volume of pores with diameters in the range of 60–350 Angstrom units is greater than 75% of the total contained pore volume. In a preferred form of the invention, the packed bulk density of the catalyst is greater than 0.50 g/cm$^3$. In fact, the prior art points to just the opposite conclusion; that such a catalyst would possess relatively low activity and selectivity, due to a deficiency of pores with diameters greater than 600 or 700 Angstroms. Therefore, the beneficial results obtained through use of the catalysts as described further below according to the instant invention were wholly unexpected.

The present invention concerns a catalyst useful in the dehydrogenation of paraffinic hydrocarbons which in one form comprises a porous aluminum oxide support and a primary catalytic component comprising one or more elements selected from the group consisting of: platinum, palladium, osmium, ruthenium, iridium, and rhodium disposed upon the support, said catalyst having a surface area greater than 100 m$^2$/g, a packed bulk density greater than 0.50 g/cm$^3$, a volume of pores with diameters below 60 Angstrom units that is less than 0.05 cm$^3$/g, a volume of pores with diameters in the range of 60–350 Angstrom units that is greater than 0.50 cm$^3$/g, and a volume of pores with diameters in the range of 60–350 Angstrom units that is greater than about 70% of the total contained pore volume.

The catalysts taught herein possess a combination of thermal stability and volumetric activity that is essentially equal to that provided by the most stable and active prior art catalysts useful in producing detergent range monoolefins from detergent range paraffins. Thus, one of the advantages of catalysts prepared according to the teachings herein is that they are especially well suited for use in a process that includes catalyst regeneration. A further advantage is that they provide better selectivity than prior art catalysts that have had comparable thermal stability and volumetric activity. Thus, the advantages of catalyst regeneration recited above can be realized in combination with excellent catalyst selectivity for the first time ever in the production of detergent range monoolefins from paraffinic starting materials. Further, in any dehydrogenation process in which the catalysts according to this invention are utilized, regardless of whether the process includes catalyst regeneration, the high volumetric activity of the catalysts prepared according to the invention can be exploited to obtain longer reaction cycles or higher average conversion in a reactor of a given size. Alternatively, reactor size can be reduced without any sacrifice of average production rate. Further, any necessary fine-tuning of the volumetric activity can easily be accomplished by varying the Pt loading. Such adjustments are well within the level of skill of one of ordinary skill in the art. The high catalyst selectivity provided by the catalysts of the invention is clearly advantageous since it can be exploited to obtain either more production at a given raw material cost per pound of product or lower raw material consumption at a given production rate. In a preferred embodiment, the catalysts of the invention provide both high catalyst selectivity and a relatively low pressure drop. A low pressure drop tends to enhance reaction selectivity by providing a lower average reaction pressure, and it may also allow the total energy consumption associated with a process to be reduced under some circumstances.

DETAILED DESCRIPTION OF PREFERRED EMBODIMENTS

This invention is concerned with the formation of monoolefins by catalytic dehydrogenation of paraffins having between 9 and 15 carbon atoms per molecule. Monoolefins so formed may subsequently be employed in the manufacture of alkylbenzene-based detergent compositions. The catalysts according to the present invention utilize known metals or combinations thereof as primary catalytic components for the dehydrogenation of paraffins, in combination with a porous alumina support selected to provide in the finished catalyst a unique specified combination of structural characteristics. In the preferred embodiment, the primary catalytic component is platinum.

The Alumina Catalyst Support

The catalysts according to the invention are supported catalysts, i.e., they comprise at least one active catalytic material that is supported on an inert carrier (the "catalyst support"). In accordance with this invention, the catalyst support is a porous alumina selected to provide in the finished catalyst specified physical properties that have been found to provide advantageous catalyst performance characteristics relating to selectivity, activity, and regenerability. The specified physical properties in a finished catalyst according to the invention include limitations upon the microstructure of the finished catalyst, including its surface area and pore structure.

It is well known that the microstructure of a finished catalyst is dependent upon the initial properties of the support material in its raw state prior to its exposure to reagents, conditions, and operations employed throughout the catalyst preparation process, some of which are well known to those in the catalyst preparation arts including impregnation with catalytically active metal(s), calcination steps, hydrothermal treatments, etc. The microstructure of the starting alumina may be altered to a considerable extent during catalyst preparation. Thus, the selection of a starting alumina for the preparation of a catalyst in accordance with the invention must properly be based upon a specification that characterizes the microstructure of the resulting finished catalyst. A starting alumina for use in catalysts prepared in accordance with the teachings of the invention can be from any source and can be made by any method, provided that the resulting finished catalyst has the unique set of physical properties specified herein. It is most preferable to use a starting alumina with a relatively narrow pore size distribution. Various methods for producing alumina with a controlled and narrow pore size distribution are known. Some of these methods have been described by D. L. Trimm and A. Stanislaus in Applied Catalysis 21, 215–238 (1986), the entire contents of which are incorporated herein by reference thereto. An especially preferred starting alumina for preparing catalysts according to this invention and obtaining the required combination of physical properties set forth herein is the type produced by Engelhard Corporation of Iselin, N.J. having the grade designation "AE-30".

Catalysts prepared in accordance with the invention have exhibited excellent selectivity in combination with a very low content of pores with diameters greater than 600 Angstrom units. For example, in catalysts B, C, E, and F described in Table I below, such pores contribute less than 10.5% of the total pore volume. According to the invention, the starting support is selected to provide a finished catalyst structure that preferably has a very low volumetric content (less than 20.00% of the total contained pore volume, including every hundredth percentage between 20.00% and 0.00%) of pores with diameters greater than 600 Angstrom units. Based upon the teachings of the prior art of this field, such a pore structure would be expected to result in undesirably low catalyst selectivity. Thus, the high selectivity obtained in accordance with the invention in the absence of a substantial amount of such large pores was wholly unexpected.

The relatively high packed bulk density (greater than 0.50 g/cm$^3$, and including every hundredth g/cm$^3$ between 0.50 and 0.80) preferred in catalysts according to one form of the invention is highly advantageous because of its favorable effect upon volumetric activity. While some prior art catalysts have had packed bulk densities comparable to those of the present invention, such prior art catalysts have been deficient in activity per unit weight, selectivity, or thermal stability. Thus, the fact that the preferred catalysts prepared in accordance with the invention have relatively high packed bulk density while maintaining excellent activity per unit weight, selectivity, and thermal stability represents a significant improvement in the art.

The Primary Catalytic Component

Catalysts prepared according to the invention contain a primary catalytic component comprising one or more elements selected from the group consisting of: ruthenium (Ru), rhenium (Rh), palladium (Pd), osmium (Os), iridium (Ir), and platinum (Pt), ("platinum group metals"). While the prior art related to dehydrogenation is fraught with patents that include claims to the use of one or more of the platinum metals in one form or another disposed upon various supports, Pt is the only metal that has been used commercially to any appreciable extent as the primary catalytic component for the dehydrogenation of detergent range paraffins. According to the present invention, it is preferred to include platinum, and it is most preferred to employ platinum and platinum alone as the primary catalytic component. However, according to the present invention, it is also possible to use other platinum group metals either alone or in various combinations as the primary catalytic component of a catalyst according to the invention. Although preferred amounts of primary catalytic component expressed as a weight percentage based on the total weight of the finished catalyst are herein specified for preferred embodiments of this invention, the use of any amount of primary catalytic component between 0.01% and 3.00% by weight based upon the total weight of the finished catalyst, including every hundredth percentage therebetween, is embraced by the scope of this invention. In any case, the primary catalytic component is disposed upon the support in such a distribution to provide catalytic surfaces that are readily accessible to the reaction mixture.

When the primary catalytic component is platinum, the platinum content of the finished catalyst expressed in units of weight percent based upon the total weight of the finished catalyst is variable and is preferably in the range of about 0.02% to 2.00%, including every hundredth percentage therebetween, more preferably between about 0.20% and 1.00%, including every hundredth percentage therebetween, more preferably still between about 0.40% and 0.70%, including every hundredth percentage therebetween, with 0.55% being most preferred. Such levels can be obtained by one of ordinary skill in the art without resorting to undue experimentation, as methods for alteration of this art-recognized variable are well known.

The Activator Component

While catalysts prepared in accordance with the present invention may include only a support and a primary catalytic component, inclusion of an activator component which functions to enhance catalyst performance characteristics is preferable. A suitable activator component may be selected from one or more of the metals scandium, titanium, vanadium, chromium, manganese, iron, cobalt, nickel, copper, zinc, yttrium, zirconium, niobium, molybdenum, silver, lanthanum, hafnium, tantalum, tungsten, rhenium, and gold. However, it is especially preferable to include an activator component that comprises one or more metals selected from the elements copper, silver, and gold (Group I-B). The primary function of an activator component as employed herein is to enhance the activity and/or selectivity of the catalyst by means of various effects upon the primary catalytic component. For example, an activator component can be used to improve the dispersion of the primary catalytic component and/or to improve the distribution of the primary catalytic component within the catalyst support pellets. To achieve the desired effect of improving catalyst activity and selectivity, the activator component must be deposited onto the catalyst support. Regardless of the activator component selected, a catalyst according to the invention may comprise any amount of activator component between 0.10% and 5.00% based upon the total weight of the finished catalyst, including every hundredth percentage therebetween. However, it is most preferred to use copper and copper alone as the activator component since copper is both highly effective as an activator and relatively low in cost. When copper is used, the concentration of copper in the finished catalyst material, expressed as a weight percentage of the total catalyst, is preferably in the range of about 0.10%–5.00%, including every hundredth percentage therebetween, more preferably between about 0.50% and 4.00%, including every hundredth percentage therebetween, more preferably still between about 1.00% and 3.00%, including every hundredth percentage therebetween, with about 2.00% being most preferable. Such levels in the finished catalyst are easily achieved by those of ordinary skill in the art without resorting to undue experimentation, through use of conventional techniques used to deposit metals onto catalyst supports as more fully described in the Examples.

Acidity Control Component

In order to provide a catalyst according to the invention which has the most favorable combination of selectivity, activity, and regenerability, it is necessary to control the acidity level of the final catalyst. If the acidity of a dehydrogenation catalyst according to this invention is too high, acid-catalyzed side reactions such as cracking and isomerization will be promoted in the dehydrogenation process to an extent that detracts from processing economics and operating efficiency. According to one form of the invention, alkali metals or mixtures thereof are preferred as acidity control agents since the oxides of these elements are basic in nature and highly effective for neutralizing the effects of various acidic species that are commonly encountered in or on the catalyst. Other metals whose oxides are known to possess an alkaline character such as the alkaline earth metals can also be used as acidity control agents, but they are less preferred than the alkalis, since they are generally less effective. Regardless of the acidity control agent(s) selected, the acidity control agent(s) are preferably added to the catalyst during its preparation using means known to those skilled in the art and as mentioned herein, and the amount of acidity control agent present on the finished catalyst may be any amount between 0.001% and 1.000% by weight based upon the total weight of the finished catalyst, including every thousandth percentage therebetween.

Some available starting aluminas already contain enough alkali, such as sodium for instance, as an impurity to provide an effective level of acidity control. Thus, the addition of an acidity control agent to the starting alumina during catalyst preparation may not be necessary in all cases. However, it is normally preferred to include an added acidity control component comprising one or more of the alkali metals in order to provide a greater degree of protection against potential catalyst acidification. If an added acidity control component is used, it is preferably deposited onto the surface of the support during catalyst preparation, using similar or the same techniques as are known in the art to be useful for depositing metals onto catalyst supports.

According to a preferred form of the invention, it is especially desirable to use added potassium as an acidity control component. When added potassium is used, the amount is preferably in the range of about 0.01%–2.00%, including every hundredth percentage therebetween, more preferably in the range of about 0.05%–1.00%, including every hundredth percentage therebetween, and more preferably still in the range of about 0.10%–0.60%, including every hundredth percentage therebetween, with about 0.20% being most preferable. In this specification and the appended claims, the amount of added potassium is expressed for convenience as a percentage by weight of metal based upon the total final catalyst weight, even though the potassium is expected to be present in the catalyst in the form of an oxide or salt. If other alkali metals or mixtures of alkali metals are added in place of potassium, appropriate amounts thereof can be readily determined using equivalent weights of the element(s) to be used without resorting to undue experimentation.

Catalyst Pellet Size and Shape

It is known to those of ordinary skill in the art of catalysis that the size and shape of catalyst pellets can be varied. Two of the most common forms in widespread use are spheres and extrudates. Catalysts previously used commercially for the dehydrogenation of detergent range paraffins have used essentially spherical porous alumina supports with average pellet diameters ranging from about 1/16 inch to about 1/8 inch. Known methods for the production of spherical alumina pellets include such methods as the agglomeration of wetted alumina powder and the oil drop method (formation of hydrogel spheres from a fluid precursor dropped into a heated oil bath). Extrudates are prepared by converting powdered alumina into an extrudable dough by various known methods and then extruding the dough through a die under suitable conditions. As the extrudate emerges from the die, it can be cut to any desired length using, for example, a rotating or reciprocating knife means at the exit point of the extruder. Extrudates having a wide variety of cross sections can be obtained by varying the shape of the die. For example, circular or trilobed cross sections are but two profiles often produced.

It is well known that pellet size and pellet shape have important effects upon the performance of a catalyst. Shorter diffusion pathways within the pellets are typically associated with higher catalyst selectivity, and the diffusion pathways can be shortened by using smaller pellets and/or by using pellet shapes that have larger surface to volume ratios. However, the effects of pellet size and shape upon the mechanical strength of the pellets and the pressure drop across a catalyst bed must also be taken into consideration. For example, smaller catalyst pellets result in a higher pressure drop, and pellet shapes other than spherical tend to result in lower mechanical strength. Thus, the optimization of pellet size and shape for a given process often requires a balancing of effects upon selectivity, pressure drop, and catalyst durability. The most favorable balance can vary significantly as the processing conditions are varied. However, for any particular case, the best balance is readily determinable by those skilled in the art through routine experimentation.

Catalyst pellets of any size and shape useful for the dehydrogenation of detergent range paraffins can be employed according to the teachings herein in the practice of the invention. If spheres are used, the preferred diameter range of the spheres is between 1.0 and 4.0 millimeters, including every tenth millimeter therebetween, with 2.5 mm being most preferable. However, for purposes of the invention, it is more preferred to use extrudates. It is preferred to use an extrudate with its longest length dimension in the range of between 1.0 and 10.0 millimeters, including every tenth millimeter therebetween. It is more preferred to use such an extrudate having an approximately circular cross section, a diameter of between about 1.0 and 4.0 millimeters, including every tenth millimeter therebetween, and a length sufficient to provide an average length to diameter ratio in the range of about 1–4. Such extrudates having an average diameter near 1.60 millimeters and an average length to diameter ratio in the range of about 2.00–4.00 (including every hundredth therebetween) are especially preferred, with an average length to diameter ratio of 3.00 being most preferred.

Properties of Finished Catalysts According to the Invention

A finished catalyst provided in accordance with this invention has a surface area that is greater than 100 $m^2/g$ and is preferably within the range 120–200 $m^2/g$, including every integral $m^2/g$ therebetween. The range 135–150 $m^2/g$, including every integral $m^2/g$ therebetween, is especially preferred.

Catalysts according to the invention may be conveniently characterized as possessing a specified volume of pores whose average diameters fall within a first range of diameters, and another specified volume of pores whose average diameters fall within a second range of diameters. The volume of pores within the second range of diameters may be further characterized in terms of the percentage of the total pore volume falling within said second range of diameters. In a catalyst according to the invention, the volume of pores having diameters below 60 Angstroms is less than 0.05 $cm^3/g$, with a volume of pores having diameters below 60 angstroms of less than 0.02 $cm^3/g$ being more preferable, and with a volume of pores having diameters below 60 angstroms of less than 0.01 $cm^3/g$ being most preferred. The volume of pores having diameters in the range 60–350 Angstroms is greater than 0.50 $cm^3/g$, and is more preferably in the range of 0.60–0.80 $cm^3/g$, including every hundredth $cm^3/g$ therebetween, with about 0.69 $cm^3/g$ being most preferred.

When expressed as a percentage of the total pore volume present in a catalyst according to one embodiment of the invention, the volume of pores with diameters in the range 60–350 Angstroms is greater than 75.00%. More preferably, the volume of pores with diameters in the range 60–350 Angstroms is greater than 80.00%. More preferably still, the volume of pores with diameters in the range 60–350 Angstroms is greater than 84.00%, with the range 86.00–89.00%, including every hundredth percentage therebetween, being the most preferable. Pore volume percentages herein are expressed as a percentage of the total pore volume of the catalyst. Measurements of pore volumes are determined by the mercury intrusion method, such method being known to those of ordinary skill in the catalyst art.

According to the conventional wisdom of the prior art, catalysts having the combination of properties (including pore distributions) possessed by the catalysts of this invention would have been expected to exhibit undesirably low catalyst selectivity. Moreover, they would have been expected to have unacceptably high diffusion resistance due to a failure to provide an adequate content of pores with diameters above about 600 or 700 Angstroms. Thus, it was surprising that catalysts according to the invention were found to have excellent selectivity with an attendant low content of large pores.

Other Finished Catalyst Properties

Other physical properties are useful in further characterization of the catalysts of this invention, including the packed bulk density. In a preferred embodiment, a catalyst in accordance with the invention has a packed bulk density greater than 0.50 $g/cm^3$. A packed bulk density in the range 0.50–0.65 $g/cm^3$, including every hundredth $g/cm^3$ therebetween, is especially preferred, with a packed bulk density of 0.57 $g/cm^3$ being most preferred. Packed bulk densities above 0.50 $g/cm^3$ tend to place limits upon both pellet density and catalyst bed void volume that tend to have favorable effects upon the volumetric activity of the catalyst.

Packed bulk densities are stated herein on the basis of measurements made by the following method. Catalyst in an amount in the range of 900–1000 ml is poured into a tared, vibrated, 1000 ml graduated cylinder. Vibration of the cylinder is continued until the volume becomes constant. The final volume of the catalyst sample is read, and the weight of the catalyst sample is determined. Packed bulk density is calculated by dividing the sample weight by the final sample volume. The measurements are made on samples that have been protected from atmospheric moisture following their final calcination during catalyst preparation.

Another characteristic of catalysts according to the invention is that they are regenerable. For purposes of this specification and the appended claims, a catalyst is "regenerable" if its response to a practical regeneration procedure is sufficiently favorable to make it economically advantageous to regenerate the catalyst at least once during its useful life. The degree of regenerability can be expressed quantitatively in terms of a cycle length reduction associated with regeneration. For purposes of this specification and the appended claims, the "cycle length reduction" attributable to a first regeneration of the catalyst is the percentage reduction in cycle length that is observed when comparing first and second operating cycles obtained with the same catalyst charge when the two cycles are conducted under conditions that are both economically viable and essentially equivalent in terms of both average paraffin conversion and other operating conditions aside from catalyst activity. In such a pair of cycles, the first cycle begins with fresh catalyst, continues without regeneration, and ends at a time selected to provide an economically-viable combination of cycle length and average paraffin conversion. The second cycle begins after the first regeneration, continues without further regeneration, and ends at a time selected to provide an average paraffin conversion about the same as that for the first cycle. In each case, idle periods within cycles are not included in the calculation of cycle length or average conversion. A preferred and/or economically viable cycle length is readily determinable by one of ordinary skill operating a catalytic process, for a given set of circumstances.

As determined by the above method, the cycle length reduction attributable to a first regeneration of a catalyst according to the invention is preferably not greater than 50% of the length of the first cycle. Catalysts according to this invention in a more preferable embodiment are characterized as having a cycle length reduction attributable to a first regeneration of not greater than 35% of the length of the first cycle. Catalysts according to this invention according to a further more preferred embodiment are characterized as having a cycle length reduction attributable to a first regeneration of not greater than 20% of the length of the first cycle.

Considering a catalyst prepared in accordance with a preferred embodiment in which the primary catalytic component is Pt, it is well known that the conditions of catalyst preparation must be adjusted to provide a catalyst with adequate mechanical strength and a high degree of Pt dispersion. According to the invention, any distribution of Pt within the support can be employed, provided that it results in a favorable Pt dispersion that has adequate thermal stability. Preferably, the Pt distribution is as uniform as possible. More particularly, the highest local concentrations of the Pt must be kept low enough to avoid excessive agglomeration of the Pt under the conditions of catalyst use and regeneration. The purity of the alumina starting material and the conditions of catalyst preparation must also be adjusted to provide adequate thermal stability of the support structure in the finished catalyst; the stability must be sufficient to avoid excessive occlusion of the Pt during the use of the catalyst. Similar considerations also apply if other metals of the platinum group are used, and these considerations are known to those skilled in the preparation and use of supported catalysts.

Catalyst Preparation

In general, many methods useful for the preparation of catalysts comprising a platinum group metal supported on alumina may be used to produce catalysts according to this invention. However, the overall processing of the catalyst precursors must conform to the teachings herein to a sufficient degree to yield a finished catalyst material having the unique combination of physical characteristics and properties (including pore size distribution) that lie within the limits defined by the claims of this invention. The novel combination of properties possessed by the catalysts described herein is necessary to provide such a catalyst material having relatively high degrees of volumetric activity, selectivity, thermal stability, and regenerability. While a preferred preparative method according to the invention is described in Example II below, substantial variations in the method of preparation can be made without departing from the metes and bounds of the claimed invention, as will be appreciated by those of ordinary skill after reading this specification and its appended claims, since many of the general principles for preparing catalysts known in the art may be used to prepare the catalysts of the invention. In any case, it is preferred to select impregnation conditions that result in favorable distributions of added components within the support as well as a high degree of dispersion of the primary catalytic component.

Catalysts prepared in accordance with a preferred form of the invention include a support, a primary catalytic component, an acidity control component, and optionally an activator component. These components are often discussed herein only in terms of the elements involved, but it is to be understood that the elements cited may be present in various oxidation states or as components of various chemical compounds or complexes at different stages of the preparation or use of the catalysts.

Various known methods for combining catalyst supports with added catalyst components during catalyst preparation are appreciated by those of ordinary skill in the art. Any of these methods that are useful in the preparation of catalysts comprising one or more platinum group metals deposited upon a porous alumina support can be used to deposit added catalyst components (including soluble metallic species, whether complexed or uncomplexed) in the preparation of catalysts according to the present invention. For example, a suitable alumina catalyst support could be immersed in a solution containing one or more heat decomposable salts of metals to be employed. The activator component and the primary catalytic component can in one embodiment be satisfactorily deposited upon the catalyst support simultaneously by using a solution containing both components. In some instances, better results are obtained if the activator component is applied first, followed by a calcination step, with the calcined material thereafter being impregnated with a solution comprising the primary catalytic component. While it is also possible to apply the primary catalytic component first followed by application of the activator component, this procedure is not usually advantageous. As described in Example II below, excellent results were obtained by a method in which an activator component and an acidity control component were simultaneously added to the support in a first impregnation step, and the primary catalytic component was subsequently added separately in a second impregnation step. In general, it is most preferable to add the primary catalytic component after any calcination step that significantly reduces the surface area of the support, in order to reduce the risk of wasteful entrapment of some or all of the primary catalytic component by the support during calcination.

While any of the heat decomposable soluble salts of the metals to be deposited on the alumina support can be employed in accordance with the invention, the best results are usually obtained by the use of salts that do not include a halogen. Halogen containing salts such as chloroplatinic acid, while usable, are not usually especially preferred because their use results in the catalyst containing at least some halogen ions, and the presence of halogen ions in the catalyst material, even in small amounts, could potentially promote undesirable side reactions. Similarly, metal sulfates are usually not advantageous because the sulfate ion is removed from the catalyst material only with difficulty, and the presence of sulfate ions in the catalyst even in small amounts can be disadvantageous. The most preferred catalyst impregnation solutions containing Group I-B metals are solutions comprising nitrates such as copper nitrate or silver nitrate dissolved in aqueous ammonium hydroxide. The most preferred solutions containing platinum metals are those prepared by dissolving diammine dinitrites such as platinum diammine dinitrite, $Pt(NH_3)_2(NO_2)_2$, or palladium diammine dinitrite, $Pd(NH_3)_2(NO_2)_2$, in aqueous ammonium hydroxide.

When an aqueous ammoniacal solution of platinum diammine dinitrite is used (as in Examples I–III below), the following method of preparing the solution gives good results. Platinum diammine dinitrite is dissolved in a hot concentrated aqueous solution of ammonium hydroxide to form a homogeneous intermediate stock solution in which the Pt concentration is somewhat higher than that intended for use in catalyst impregnation. The stock solution may then optionally be held at a temperature in the range of about 65–85° C. ("aged") for a period of up to about four hours, resulting in some approach toward equilibrium of the distribution of complexes present in the solution. The amount of solution needed for catalyst impregnation is conveniently provided by diluting an appropriate quantity of intermediate stock solution with deionized water while maintaining a temperature suitable for maintaining homogeneity, such as about 65° C. If desired, the diluted solution can be heated or cooled to a somewhat different temperature for the catalyst impregnation step. In any case, it is highly preferable that the solution is homogeneous when brought into contact with the catalyst support. It will be appreciated by those skilled in the art that the most preferred method of preparation may vary, depending, e.g., on the desired size of the catalyst particles. It belongs to the skill of the skilled person to select the most suitable method and solution concentrations for a given set of circumstances.

During a given impregnation step, the amount of solution employed can be varied widely. It is preferred to use a sufficiently large volume of solution to permit uniform deposition of the metal salts. A very satisfactory procedure has been found to be to use that volume of solution in each instance which is equal to the amount required to fully saturate the support material. According to this procedure, the amount of metal deposited upon the support during an impregnation step is simply equal to the entire amount of metal present in the solution that is used for the impregnation step. The amount of solution required to saturate the support material can be readily determined by tests conducted on a small sample of the support material. If a selected metal salt (such as a basic carbonate, as but one example) in any instance is not sufficiently soluble to permit the desired amount of the metal to be deposited in a single application, the metal can be applied in a plurality of steps, with the catalyst material being dried and/or calcined between such steps.

In various examples provided herein, calcination conditions are described in terms of a particular calcination temperature and either a specified calcination time or a calcination time sufficient to produce a stated effect. It is appreciated by those skilled in this art that somewhat different calcination temperatures could also be used with essentially equivalent results. In some cases, compensating adjustments of calcination time might be required, as such adjustments are well known in the art. When the calcination is carried out to achieve catalyst particles having a particular surface area, the progression of the change in surface area may be readily monitored by testing samples of the material at appropriate intervals using techniques known to those skilled in the art, such as the BET method with nitrogen as the adsorbed species. When treatment at elevated temperatures is employed to eliminate volatile or decomposable impregnation by-products such as nitrites, nitrates, ammonia, etc., similar testing of small quantities of catalyst pellets at selected intervals may be undertaken to assure success, or alternatively, those skilled in the art may employ with confidence those conditions well known and recognized as sufficient for such elimination, provided the finished catalyst possesses the physical limitations set forth in the claims herein. While calcination in air is indicated in various examples, the present invention also contemplates the use of other atmospheres during calcination, since the use of other atmospheres, including oxidizing, reducing, and inert atmospheres is known to artisans of ordinary skill in catalyst calcination. Calcination is conventionally carried out at a temperature between 300 and 1200 degrees Centigrade, preferably between 400 and 1000 degrees C., including every degree of temperature therebetween. The duration of calcination treatment may be any amount of time between 0.5 and 24 hours, but is preferably between forty five (45) minutes and 4 hours. It will be appreciated that the average temperature during the calcination will be higher than the average temperature during any drying treatment.

EXAMPLE I

Prior Art

This example illustrates the preparation and use of an alumina-supported dehydrogenation catalyst according to what is known in the prior art. As used herein, all parts are by weight, unless otherwise indicated. The alumina support employed was obtained from LaRoche Industries, Inc., grade A-302, 5–8 mesh spheres. Specifications for this support include a bulk density of at least 0.673 g/cm$^3$, a surface area of at least 270 m$^2$/g, and a macropore volume of at least 0.18 cm$^3$/g. Into a suitable catalyst coating pan was charged 104.6 parts of this catalyst support. A first impregnation solution was prepared from 0.666 parts of potassium nitrate, 8.23 parts of cupric nitrate trihydrate, 23.0 parts of concentrated aqueous ammonium hydroxide (28% $NH_3$), and a sufficient amount of deionized water to provide a final solution volume equal to that required to fill the pores of the support, as determined by a test on a small sample of the alumina. As the support was tumbled in the coating pan, the entire first impregnation solution was sprayed onto the pellets over a period of about seven minutes. After a few more minutes of tumbling sufficient to allow complete absorption of the solution by the pellets, the pellets were dried at 138° C. to a moisture content of 3% or less, and then calcined in air at about 675° C. for a time sufficient to reduce their surface area to the range 180–220 m$^2$/g, as determined by tests on small samples performed during the progress of the calcination. After cooling to ambient temperature and screening to remove fines, the resulting calcined intermediate pellets were again placed in a coating pan and impregnated a second time with a hot (50–60° C.) aqueous ammoniacal solution of platinum diammine dinitrite containing 0.37 parts of platinum, using a procedure analogous to that for the first impregnation. The resulting pellets were subsequently dried at 113° C. to a moisture content of 5% or less and then calcined in air at about 455° C. for a time sufficient to eliminate decomposable impregnation by-products such as nitrites and nitrates. Finally, the pellets were cooled and screened to obtain 100 parts of finished catalyst. The resulting catalyst had the following measured properties: 0.25% K, 2.1% Cu, 0.37% Pt, and surface area 218 $m^2/g$. Some additional properties that are typical for a conventional catalyst of this type can be found in Table I below (Catalyst A).

This catalyst was tested by using it for the dehydrogenation of a normal paraffin mixture that contained hydrocarbons that comprised 10, 11, 12 and 13 carbon atoms per molecule in a laboratory recycle reactor under the following conditions: catalyst temperature 444–445° C., pressure 7.9–8.1 psig, hydrogen to hydrocarbon mole ratio 0.69–0.71, paraffin feed rate 79–80 g/g catalyst/hr, and run length five hours. The range of normal paraffin conversion obtained was 7.5–11.0%, and the range of conversion to aromatic by-products was 1.02–1.93%.

EXAMPLE II

This example illustrates the preparation and use of an alumina-supported dehydrogenation catalyst according to the present invention. The procedure of Example I was repeated except that the support employed was Engelhard Corporation grade AE-30 extrusions having approximately circular cross section with diameters of about $\frac{1}{16}$ inch and length to diameter ratios predominantly within the range 2–4. The duration of the first calcination was selected to be at least that length of time sufficient to eliminate decomposable impregnation by-products, and the amount of platinum in the second impregnation solution was increased to provide a higher platinum content in the finished catalyst. The total amount of support used, and amounts of the cupric and potassium nitrates employed in the first impregnation solution were reduced slightly as required to provide a resulting catalyst having the following properties: 0.23% K, 2.07% Cu, 0.54% Pt, surface area 144 $m^2/g$, packed bulk density 0.57 $g/cm^3$, macropore volume 0.06 $cm^3/g$, total pore volume 0.78 $cm^3/g$, a pore volume of zero for pores with diameters below 60 Angstroms, and a pore volume of 0.69 $cm^3/g$ for pores with diameters in the range 60–350 Angstroms (equal to 88.5% of the total pore volume).

The dehydrogenation performance of this catalyst was tested using the same feedstock and conditions as those used in Example I. The range of normal paraffin conversion obtained was 10.9%–15.5%. The conversion increase compared to Example I was proportional to the increase in the weight of Pt in the reactor. Thus, there was no loss of Pt utilization efficiency at the higher Pt level. The range of conversion to aromatic by-products was 1.23–2.44%. At a given paraffin conversion, the conversion to aromatic by-products was 36% lower than it was in Example I. Thus, the selectivity of a catalyst according to the present invention was found to be much better than that of the prior art catalyst of Example I.

EXAMPLE III

The procedure of Example II was repeated except that a different support lot was used. The catalyst obtained had the following properties: 0.27% K, 2.08% Cu, 0.52% Pt, surface area 143 $m^2/g$, packed bulk density 0.56 $g/cm^3$, macropore volume 0.07 $cm^3/g$, total pore volume 0.78 $cm^3/g$, a pore volume of zero for pores with diameters below 60 Angstroms, and a pore volume of 0.68 $cm^3/g$ for pores with diameters in the range 60–350 Angstroms (equal to 87.2% of the total pore volume). The range of normal paraffin conversion obtained was 10.8–15.3%, and the range of conversion to aromatic by-products was 0.92–2.17%. At a given paraffin conversion, the conversion to aromatic by-products was 51% lower than it was in Example I. This further illustrates the selectivity advantage of the catalyst of the present invention compared to the prior art catalyst of Example I.

EXAMPLE IV

The procedure of Example II was repeated except that the support employed was a different type of $\frac{1}{16}$ inch extrusion that provided a much higher surface area in the finished catalyst. The resulting catalyst had the following properties: 0.32% K, 2.19% Cu, 0.65% Pt, surface area 297 $m^2/g$, macropore volume 0.07 $cm^3/g$, total pore volume 0.77 $cm^3/g$, a pore volume of 0.20 $cm^3/g$ for pores with diameters below 60 Angstroms, and a pore volume of 0.48 $cm^3/g$ for pores with diameters in the range 60–350 Angstroms (equal to 62.3% of the total pore volume). The range of normal paraffin conversion obtained was 9.3–14.6%, and the range of conversion to aromatic by-products was 1.1–3.0%. At a given paraffin conversion, the conversion to aromatic by-products was about 20% lower than it was in Example I. This 20% reduction in aromatics formation is substantially smaller than the reductions of 36% and 51% seen in Examples II and III. This illustrates the less favorable selectivity that is obtained when the pellet diameter is the same as that in Examples II and III but the pore size distribution of the catalyst is not in accordance with the invention.

EXAMPLE V

Two catalysts were prepared from different portions of the same lot of Kaiser KA 101 alumina pellets. For Catalyst S (standard surface area), the pellets were calcined at 600° C. for 2 hours to produce modified pellets with surface area 190 $m^2/g$, macropore volume 0.18 $cm^3/g$, and bulk density 0.67 $g/cm^3$. The modified pellets were impregnated with an aqueous ammoniacal solution of platinum diammine dinitrite and cupric nitrate, dried at 120° C., and calcined at 450° C. for two hours to obtain a finished catalyst containing 0.45% Pt and 2.0% Cu. This catalyst was tested by using it for the dehydrogenation of normal dodecane in a laboratory plug flow reactor under the following conditions: catalyst temperature 450° C., pressure 10 psig, hydrogen to hydrocarbon mole ratio 8.0, dodecane feed rate 32 volumes of liquid per volume of catalyst bed per hour, and run length 25 hours. The range of normal paraffin conversion obtained was 13.0–14.3%, and the range of conversion to aromatic by-products was 0.21–0.56%.

For Catalyst L (low surface area), the pellets were calcined at 1000° C. for 6 hours to produce modified pellets with surface area 48 $m^2/g$, macropore volume 0.25 $cm^3/g$, and bulk density 0.69 $g/cm^3$. Conversion of the modified pellets to catalyst, resulting levels of Pt and Cu, and the conditions for catalyst testing were all the same as for Catalyst S except that a higher catalyst temperature was used during part of the dehydrogenation run. For Catalyst L, the run began at 460° C. in an attempt to match the conversion obtained with Catalyst S. However, in spite of the higher temperature, the highest conversion obtained was only 14.0%. Thus, the volumetric activity of Catalyst L was substantially lower than that of Catalyst S. After 2 hours, the temperature was reduced over a period of 3 hours to 450° C., and this temperature was then maintained for the remainder of the run. The range of normal paraffin conversion obtained at 450° C. was 9.1–11.3%. The range of conversion to aromatic by-products for the entire run was 0.04–0.30%. These results show that while the catalyst selectivity is improved by calcining the prior art support to a lower surface area as taught in U.S. Pat. No. 3,920,615, the selectivity improvement is accompanied by a substantial reduction in the activity obtained from a given weight of Pt. This disadvantage is avoided in the catalyst of the present invention, as illustrated in Example II.

EXAMPLE VI

Samples of the catalyst of Example II and a prior art catalyst prepared as described in Example I were aged for two hours under nitrogen at 540° C. The dehydrogenation performance of each catalyst before and after aging was tested using the same feedstock and conditions as those used in Example I. Paraffin conversions after 100 minutes of operation were used for comparisons. For the catalyst of Example II, the indicated result of the aging was to reduce the conversion from 12.6% to 11.4%, a reduction of 9.5% of the conversion obtained without the aging. For the other catalyst, the indicated result of the aging was to reduce the conversion from 9.7% to 9.0%, a reduction of 7.2% of the conversion obtained without the aging. It is concluded that both catalysts exhibited excellent thermal stability. The small difference between the two results is considered to be insignificant.

EXAMPLE VII

The procedure of Example II was repeated except that the order of addition of the metals was changed. In the first impregnation step, only the potassium was added instead of both the potassium and the copper. In the second impregnation step, both the copper and the platinum were added instead of only the platinum. The resulting catalyst had the following properties: 0.37% K, 2.66% Cu, 0.76% Pt, surface area 123 m$^2$/g, packed bulk density 0.58 g/cm$^3$, macropore volume 0.05 cm$^3$/g, total pore volume 0.78 cm$^3$/g, a pore volume of zero for pores with diameters below 60 Angstroms, and a pore volume of 0.69 cm$^3$/g for pores with diameters in the range 60–350 Angstroms (equal to 88.5% of the total pore volume). The range of normal paraffin conversion obtained was 9.5–13.0%, and the range of conversion to aromatic by-products was 0.98–2.04%. At a given paraffin conversion, the conversion to aromatic by-products was 32% lower than it was in Example I. This illustrates a variation in the catalyst preparation method that can occur within the scope of the invention without any substantial sacrifice in selectivity.

EXAMPLE VIII

The procedure of Example II was repeated except that the diameter of the support was increased from about 1/16 inch to about 1/8 inch. The resulting catalyst had the following properties: 0.25% K, 2.1% Cu, 0.54% Pt, surface area 133 m$^2$/g, packed bulk density 0.54 g/cm$^3$, macropore volume 0.07 cm$^3$/g, total pore volume 0.78 cm$^3$/g, a pore volume of zero for pores with diameters below 60 Angstroms, and a pore volume of 0.68 cm$^3$/g for pores with diameters in the range 60–350 Angstroms (equal to 87.2% of the total pore volume). The range of normal paraffin conversion obtained was 7.8–11.6%, and the range of conversion to aromatic by-products was 0.92–1.92%. At a given paraffin conversion, the conversion to aromatic by-products was 17% lower than it was in Example I. This illustrates a selectivity advantage for the catalyst of the invention over the prior art catalyst of Example I in the absence of any significant difference in pellet diameter.

EXAMPLE IX

A single stage, adiabatic, plug flow reactor with downward flow was charged with two types of catalyst in separate layers. Catalyst P was used for the lower layer, and Catalyst N was used for the upper layer. By weight, the resulting hybrid catalyst bed contained 75.7% Catalyst P and 24.3% Catalyst N. Catalyst P was a prior art catalyst prepared as described in Example I, and Catalyst N was prepared in accordance with the invention. Catalyst P had the following properties: 0.24% K, 1.8% Cu, 0.46% Pt, surface area 213 m$^2$/g, and packed bulk density 0.74 g/cm$^3$. Catalyst N had the following properties: 0.30% K, 1.8% Cu, 0.54% Pt, surface area 142 m$^2$/g, and packed bulk density 0.58 g/cm$^3$. In a first operating cycle, the hybrid catalyst bed was used for the dehydrogenation of normal paraffin under conditions within the following ranges: catalyst bed inlet temperature 429–454° C., inlet pressure 8.3–10.0 psig, hydrogen to hydrocarbon mole ratio 0.47–1.06, paraffin feed rate 4.9–5.3 g/g catalyst/hr, and paraffin conversion range 8.25–11.90%. The cycle length was 32 days (23 days on C10–13 paraffin and 9 days on C11–14 paraffin), and the average paraffin conversion was 10.72%. After the first cycle, the catalyst was regenerated by burning off accumulated coke, hydrogen treated, and then used for a second operating cycle. In the second cycle, the ranges of the operating conditions were as follows: catalyst bed inlet temperature 437–454° C., inlet pressure 7.6–10.6 psig, hydrogen to hydrocarbon mole ratio 0.33–1.11, paraffin feed rate 4.9–5.3 g/g catalyst/hr, and paraffin conversion 7.90–12.10%. The cycle length was 29 days (20 days on C10–13 paraffin and 9 days on C11–14 paraffin), and the average paraffin conversion was 10.54%. Comparison of the two cycles indicates that the regeneration restored a large fraction of the catalyst activity that had been lost during the first cycle. Furthermore, the cycle length and average conversion for the second cycle were well within practical operating ranges. Thus, the hybrid bed gave no indication of any deficiency of regenerability, and the results indicate an acceptable degree of regenerability for the catalyst of the invention.

Structural Details

The data in Table I below is presented for the purpose of a more detailed discussion of the effects of certain structural variations in finished catalysts. Catalyst A represents the best known regenerable catalyst in the prior art for the dehydrogenation of detergent range paraffins. The indicated aromatics reduction of zero is based upon the result obtained in Example I, and the other properties were determined using another representative sample that had been prepared by the method of Example I. Catalysts B–F are the catalysts of Examples II, III, IV, VII, and VIII respectively. In all cases, higher aromatics reduction is equivalent to higher catalyst selectivity.

Catalysts B, C, E, and F were all prepared in accordance with the invention. For each of these catalysts, the selectivity is substantially higher than that for the prior art Catalyst A. Compared to Catalysts B and C, Catalyst E has slightly lower selectivity, apparently because it was prepared using a less optimal order of metals addition. Compared to Catalysts B and C, Catalyst F has lower selectivity because of its larger pellet diameter. Compared to Catalyst A, Catalyst F has a slightly smaller pellet diameter, but the resulting diffusional advantage is more than offset by its greater pellet length. Thus, it is readily apparent that a selectivity advantage at least as large as that indicated in the table for Catalyst F in comparison to Catalyst A results from a more favorable pore structure in Catalyst F.

Catalyst D is not in accordance with the invention since the pore volume for diameters below 60 Angstroms does not fall within the required range. Compared to Catalyst A, Catalyst D has better selectivity because of its smaller pellet diameter. However, since Catalysts B, C, and D have very similar pellet shapes and diameters, the lower selectivity of Catalyst D compared to Catalysts B and C demonstrates clearly that the pore structure of Catalyst D is less favorable.

The comparisons discussed above show that the pore structures of Catalysts B, C, E, and F prepared in accordance with the invention provide higher selectivity than the pore structures seen in Catalysts A and D. For Catalysts B, C, E, and F, the much lower content of pores with diameters below 60 Angstroms is evidently a very important contributor to higher selectivity. In Catalyst A, the much higher content of macropores (>700 Angstroms) is unable to compensate for the adverse selectivity impact of a relatively high content of pores smaller than 60 Angstroms. This ineffectiveness of macropores was quite surprising and unexpected in view of the prior art teaching that substantial volumes of pores with diameters greater than 600 or 700 Angstroms are associated with better selectivity. For example, in U.S. Pat. No. 4,608,360, it is required that at least 55% of the total pore volume of the catalyst must be associated with pores having mean diameters of about 600 Angstroms or larger.

to properly stabilize the finely dispersed platinum crystallites that are needed for high catalytic activity. Thus, in a catalyst with a high content of very large pores, increasing the platinum loading in order to provide higher initial activity tends to crowd the crystallites so close together that the thermal stability of the platinum dispersion is adversely affected. A further disadvantage of very large pores is their tendency to reduce the mechanical strength of the catalyst pellets.

In Catalysts B, C, E, and F, a very high content of pores in the 60–350 Angstrom range is not associated with low selectivity. Thus, it is concluded that pores within this range are surprisingly able to contribute very effectively to the low diffusion resistance that is needed for high selectivity.

Another surprising aspect of the catalysts of this invention which will undoubtedly be appreciated by those skilled in the art upon their reading and understanding this disclosure is the great extent to which it was possible to reduce the content of micropores, defined here as pores with diameters smaller than 60 Angstroms. Some of the catalysts prepared in accordance with the invention were essentially devoid of such micropores. While it was known previously that selectivity could be improved by means of more severe calcination, apparently due to a reduction in the content of micropores, all earlier attempts in this direction gave relatively unfavorable results. If the calcination was sufficiently severe to provide a large selectivity improvement, the surface area was reduced so much that the activity and thermal stability were undesirably low. If the calcination was less severe, the selectivity improvement was smaller than desired. Now it has been found that a very high degree of micropore reduction and selectivity improvement can be

TABLE I

Selected Catalyst Properties

| Catalyst | A | B | C | D | E | F |
|---|---|---|---|---|---|---|
| Cu Content, % | 1.9 | 2.07 | 2.08 | 2.19 | 2.66 | 2.1 |
| Pt Content, % | 0.34 | 0.54 | 0.52 | 0.65 | 0.76 | 0.54 |
| K Content, % | 0.19 | 0.23 | 0.27 | 0.32 | 0.37 | 0.25 |
| Surface Area (m$^2$/g) | 209 | 144 | 143 | 297 | 123 | 133 |
| Cumulative Pore Volume (cm$^3$/g) | | | | | | |
| up to 30 Angstroms pore diam. | 0.02 | 0.00 | 0.00 | 0.00 | 0.00 | 0.00 |
| up to 60 Angstroms pore diam. | 0.20 | 0.00 | 0.00 | 0.20 | 0.00 | 0.00 |
| up to 90 Angstroms pore diam. | 0.28 | 0.03 | 0.03 | 0.51 | 0.00 | 0.02 |
| up to 120 Angstroms pore diam. | 0.30 | 0.22 | 0.19 | 0.60 | 0.07 | 0.14 |
| up to 200 Angstroms pore diam. | 0.32 | 0.62 | 0.63 | 0.65 | 0.57 | 0.58 |
| up to 350 Angstroms pore diam. | 0.33 | 0.69 | 0.68 | 0.68 | 0.69 | 0.68 |
| up to 600 Angstroms pore diam. | 0.34 | 0.72 | 0.70 | 0.70 | 0.72 | 0.70 |
| up to 700 Angstroms pore diam. | 0.34 | 0.72 | 0.71 | 0.70 | 0.73 | 0.71 |
| up to 1000 Angstroms pore diam. | 0.35 | 0.74 | 0.73 | 0.72 | 0.74 | 0.72 |
| up to 10000 Angstroms pore diam. | 0.47 | 0.76 | 0.75 | 0.74 | 0.76 | 0.76 |
| Total Pore Volume (cm$^3$/g) | 0.54 | 0.78 | 0.78 | 0.77 | 0.78 | 0.78 |
| Pore Volume >700 Angstroms | 0.20 | 0.06 | 0.07 | 0.07 | 0.05 | 0.07 |
| Pore Volume <60 Angstroms | 0.20 | 0.00 | 0.00 | 0.20 | 0.00 | 0.00 |
| Pore Volume, 60–350 Angstroms | 0.13 | 0.69 | 0.68 | 0.48 | 0.69 | 0.68 |
| Average Pellet Diameter, Inch | 0.12 | 0.06 | 0.06 | 0.06 | 0.06 | 0.11 |
| Aromatics Reduction, % | 0 | 36 | 51 | 16–25 | 32 | 17 |

Elimination of the prior strong reliance upon very large pores (larger than 600 Angstroms) in accordance with the teachings of the invention is advantageous because of some inherent disadvantages of very large pores. Compared to smaller pores, very large pores contain a great volume of empty space that can now be viewed as wasted space, since it is no longer found to be necessary for high reaction selectivity. On a per unit catalyst volume basis, very large pores provide less of the support surface area that is needed obtained in combination with a final surface area high enough to provide both high activity and high thermal stability.

The packed bulk density of the catalyst of the invention is higher than that of most prior art dehydrogenation catalysts. This property in combination with a novel pore structure makes it possible to obtain a very high level of volumetric activity, without any significant sacrifice in thermal stability or selectivity. The high bulk density, low macropore volume, and low micropore volume result in a previously unavailable high level of favorably situated support surface area per unit reaction volume. This makes it possible to introduce a larger amount of platinum into a reactor of a given size without any significant sacrifice of average effectiveness per unit weight of platinum.

Useful Process Characteristics

Any of the various combinations of equipment, raw materials, and operating conditions that can be used with prior art catalysts for the production of detergent range monoolefins by the dehydrogenation of paraffins can also be used with the catalysts of this invention. However, it is preferred to use a process that includes regeneration of the catalyst at economically advantageous intervals. In the following sections, various preferred process characteristics are described for a process that includes catalyst regeneration.

Reactor Design

For the practice of this invention, the reactor or reactors employed should preferably be designed for adiabatic plug flow operation. One reason for this is that exposure of higher conversion reaction mixtures to hotter walls tends to lower reaction selectivity. Another reason is that exposure of such mixtures to the higher catalyst temperatures existing near the inlet of an adiabatic reactor tends to both lower reaction selectivity and cause an unacceptably high rate of catalyst deactivation under the conditions of this process. Another reason is that selectivity tends to be highest when each increment of conversion occurs at the lowest possible average olefin to paraffin ratio, i.e. when back-mixing is minimized. A fourth reason is that the portion of an adiabatic reactor downstream of the region where most of the conversion occurs provides a favorable lower temperature environment in which the preferred excess initial catalyst activity can reside.

Any other elements of reactor design suitable for use in platinum catalyzed dehydrogenation of detergent range paraffins can also be utilized in the practice of this invention. The direction of flow can be down flow, up flow, or radial flow. The ratio of bed depth in the direction of flow to the bed cross sectional area at a particular depth can vary widely. The catalyst bed can be fixed or moving, but it should not be fluidized since that would be incompatible with plug flow operation.

It is preferred to use continuous, fixed bed, down flow cylindrical reactors with a ratio of length over diameter selected to minimize problems with wall effects, channeling, excessive back mixing, excessive thermal feedback, or insufficient turbulence outside the catalyst pellets. It is also preferred that the paraffin feed be completely vaporized and uniformly mixed with added hydrogen prior to contact with the catalyst bed.

Paraffin Feedstock

The detergent range paraffin utilized as a feedstock can be from any source and of any grade suitable for use in platinum catalyzed dehydrogenation. Paraffins useful as feedstocks for dehydrogenation using the catalysts of this invention include all paraffins having between 2 and 20 carbon atoms per molecule, whether they be straight chain or branched. While it is believed that any paraffin that is generally recognized as being capable of undergoing catalytic dehydrogenation is suitable for use in accordance with the invention, paraffins suitable for the production of alkylbenzenes as an intermediate in the production of sulfonated alkylbenzenes for detergent use are a preferred feedstock, and normal paraffins are an especially preferred feedstock. "Detergent range paraffin" means paraffins with total carbon numbers in the range 9 to 15 inclusive, i.e., saturated hydrocarbon molecules which contain 9, 10, 11, 12, 13, 14, or 15 carbon atoms per molecule. Total carbon numbers within the range 10 to 14 are especially preferred. Mixtures containing a range of carbon numbers can be used, and it is preferred to limit the breadth of the carbon number range in such mixtures to four carbons or less. The paraffins utilized can be fresh (not previously used in the dehydrogenation process) or recycled (unconverted paraffin recovered from an earlier dehydrogenation product). Mixtures containing fresh and recycled paraffins in any proportions can also be used.

As various ranges are specified in this specification and the claims appended hereto, it is beneficial to define all ranges set forth as having specified limits as including those values which are at the extremity of the range specified. For example, the words "any number of carbon atoms between 9 and 15" means 9, 10, 11, 12, 13, 14, and 15. Similarly, percentage ranges also include the extremity values used to define the range.

Number of Stages and Amount of Catalyst

It is preferred to use either a single reaction stage or two stages in series with a suitable reheating means between the stages. If two stages are used, various aspects of the reactor designs and operating conditions can be alike or different. In the preferred method of operation, a series of many operating cycles and intervening catalyst regenerations can be completed without any interruption for the addition or removal of catalyst. At the beginning of such a series, the types and amounts of catalyst loaded into the reactor or reactors should be such that a large excess of catalyst activity is present. Such excess initial activity is needed to compensate for catalyst deactivation that occurs both within operating cycles and from cycle to cycle. The preferred amount of excess initial activity is the amount that provides the most favorable balance among the lengths of cycles, the number of cycles in a series, and the overreaction tendency experienced at the beginning of each cycle due to the excess activity.

Paraffin Conversion

Any degree of conversion per pass and any means of controlling conversion that are suitable for the platinum catalyzed dehydrogenation of detergent range paraffins can be utilized in the practice of this invention. Conversion across one stage could be very low in some cases, for example about 1%. Total conversion across all stages of the dehydrogenation process could be as much as 20% or higher. The preferred range of paraffin conversion across all stages combined is from about 5% to about 20%. Conversion can be held nearly constant during a processing cycle or varied in any desired manner. The best schedule for adjustments of conversion based upon time within an operating cycle depends significantly upon the other conditions in use, and it can be determined by routine experimentation.

Various methods of controlling conversion within a processing cycle are well known. Such methods include adjustments of reaction temperature, reversible catalyst poisoning as described in U.S. Pat. No. 3,632,662, and intermittent or continuous addition of catalyst during processing. Any such means can be used in the practice of this invention. In the preferred method, processing cycles begin with a substantial excess of catalyst bed activity and operating conditions toward the beginning of a cycle are limited to relatively low temperature ranges that provide a high tolerance for excess catalyst activity. Good results can be obtained in this manner without reliance upon either reversible poisoning or catalyst addition during processing.

Catalyst Regeneration and Hydrogen Treatment

The preferred method for catalyst regeneration is to burn off the accumulated coke using a dilute oxygen source such as a mixture of air with nitrogen and/or recycled coke combustion products. Oxygen level and inlet gas temperature can be adjusted to provide an appropriate peak temperature within the coke burning zone. In the preferred method of operation, after the coke has been burned off and prior to the introduction of the paraffin feed, the catalyst is treated with pure or recycled hydrogen for about an hour or more at a temperature comparable to that to be used at the beginning of the next processing cycle. Hydrogen treatment is also used to prepare new catalyst for use. Specific conditions for catalyst regeneration and hydrogen treatment under any particular circumstances can be determined by routine experimentation.

Added Hydrogen

It is known in the conventional commercial dehydrogenation of detergent range paraffins to include some amount of added hydrogen in the dehydrogenation feed mixture in order to maintain the catalyst in an active state. While not bound by any theory, it is generally believed that the effects of hydrogen go beyond simple dilution effects. In particular, hydrogen is believed to play a role in suppressing formation of coke upon catalyst surfaces and in maintaining the platinum in the necessary metallic state.

The amount of added hydrogen can be varied widely, and the $H_2$:HC ratio can be constant or varied within a reaction cycle. The $H_2$:HC ratio is defined herein as the molar ratio of added hydrogen to detergent range hydrocarbons in the feed mixture. Although much higher ratios can be used, it is preferred to use relatively low $H_2$:HC ratios within the range of about 0.3 to 1.9. It is especially preferred to use $H_2$:HC ratios within the range of about 0.4 to 1.0. Among the advantages of relatively low $H_2$:HC ratios are smaller equipment sizes, lower energy costs, and the ability to operate effectively at lower temperatures. Lower operating temperatures are particularly advantageous near the beginning of operating cycles when large amounts of excess catalyst activity are present.

The hydrogen utilized in the present invention can be from any source and of any grade suitable for use in platinum catalyzed dehydrogenation of paraffins. Suitable types include hydrogen produced by another process; hydrogen generated within the dehydrogenation process, separated, and recycled; and hydrogen of varying purity. For economic reasons, it is usually preferred to use hydrogen generated within the process. The extent of purification or treatment of recycle hydrogen prior to its reuse should be selected to optimize overall process efficiency.

Temperature and Pressure

Any catalyst bed inlet temperatures suitable for platinum catalyzed dehydrogenation of detergent range paraffins can be used in the practice of this invention. For operations with a single reaction stage, it is preferred to use inlet temperatures that do not exceed 460° C. For operations with two or more reaction stages, it is preferred to use inlet temperatures that do not exceed 450° C. Among the advantages of such temperature limits are reduced yield loss to cracking reactions, lower energy costs, reduced coke formation rates, lower equipment maintenance costs, and improved catalyst effectiveness.

For best results, it is usually necessary to vary the inlet temperature within an operating cycle. Typically the lowest temperature is used at the beginning of a cycle to suppress overreaction, and higher temperatures are used later to compensate for declining catalyst activity. At each time within an operating cycle, the inlet temperature required for a particular reaction stage depends strongly upon the increase in conversion desired across the stage, the conversion desired at the outlet of the stage, the total pressure, and the $H_2$:HC ratio, all of which interact with the inlet temperature to determine whether the temperature at the exit of the stage will be high enough to allow the desired conversion to be reached before further conversion is prevented by the effects of the reaction equilibrium. For any particular situation, the optimal schedule for adjustments of inlet temperatures can be determined by routine experimentation by one skilled in the art in view of the present disclosure.

Any total pressure suitable for the platinum catalyzed dehydrogenation of detergent range paraffins can be utilized in the practice of this invention. It is preferred that the pressure be at least one atmosphere because of extra costs and hazards associated with operation at sub-atmospheric pressures. It is also preferred to use pressures below about three atmospheres because of chemical equilibrium advantages. It is especially preferred that pressures in a final reaction stage be as low as practicable, i.e. from about 1 atmosphere to about 1.8 atmospheres.

WHSV

The weight hourly space velocity (WHSV) is defined herein as the weight of paraffin feedstock entering a particular catalyst bed per hour per unit weight of catalyst in that bed (both weights being measured in the same units). As WHSV is increased, conversion across a catalyst bed of a given activity tends to decrease. Selecting a value of WHSV also fixes the value of such alternative parameters as liquid hourly space velocity (LHSV) or contact time. Any WHSV suitable for platinum catalyzed dehydrogenation of detergent range paraffins can be utilized in the practice of this invention. Values in the range from about 1 to about 20 are preferred. The best value for use in any particular situation can be determined by routine experimentation in view of the present disclosure.

Operating Cycles

The operation of a process with a particular catalyst bed from the time it is loaded or regenerated until it is removed or again regenerated is designated herein as an operating cycle. The length of such a cycle refers to the time that was spent processing the feedstock and does not include idle periods. The length of a cycle can be varied widely, and the most favorable cycle length depends significantly upon both the catalyst age at the beginning of the cycle and the operating conditions employed during the cycle. While any cycle length can be used, it is preferred to use cycle lengths greater than about 200 hours since shorter cycles tend to excessively reduce the percentage of time that a reactor is available for processing of paraffin. Much longer cycles are possible, for example 1000 hours or longer. As the cycle length increases, it becomes more difficult to maintain conversion and operating conditions within optimal ranges as the catalyst deactivates.

Product Recovery and Use

The olefins produced in accordance with this invention can be recovered or utilized in any suitable manner. Suitable uses include conversion to alkylbenzenes for use in detergents and conversion to various other products. Suitable methods of product recovery include various effective combinations of steps selected from condensation, gas-liquid separation, fractional distillation, selective adsorption, solvent extraction, and selective chemical reactions. In the preferred method, the gaseous dehydrogenation reaction mixture is cooled to produce a hydrocarbon rich liquid phase and a hydrogen rich gaseous phase. The gaseous phase is partly vented and partly recycled, with or without further refinement, to the dehydrogenation process. The liquid phase is optionally subjected to selective hydrogenation for conversion of diolefins to monoolefins and is in any case fractionated to remove low boiling cracking products. The remaining mixture comprising detergent range olefins and paraffins is contacted with benzene and an acidic catalyst under suitable alkylation conditions to convert the olefins mainly to alkylbenzene. The alkylation mixture is then separated by suitable means including fractional distillation into a product alkylbenzene fraction, an unconverted paraffin fraction, an unconverted benzene fraction, and other components such as recovered catalyst and various by-products. The benzene and paraffin fractions are recycled, with or without further refinement or removal of purge streams, to the alkylation and dehydrogenation steps respectively. In a particularly preferred method, the acidic alkylation catalyst is hydrofluoric acid which is recovered from the alkylation mixture, at least partially purified, and recycled to the alkylation step.

Although this invention has been shown and described with respect to certain preferred embodiments, it is obvious that equivalent alterations and modifications will occur to others skilled in the art upon reading and understanding of this specification and the appended claims. The present invention includes all such modifications and alterations, and is limited only by the scope of the following claims.

I claim:

1. A process for forming an olefin by dehydrogenation of a hydrocarbon which comprises the steps of:
   a) providing a hydrocarbon;
   b) providing a catalyst comprising a primary catalytic component that comprises one or more elements selected from the group consisting of: platinum, rhodium, iridium, palladium, ruthenium, and osmium deposited on a solid support comprising porous alumina, wherein said regenerable catalyst has a surface area greater than 100 m²/g, a volume of pores with diameters below 60 Angstrom units that is less than 0.05 cm³/g, a volume of pores with diameters in the range of 60–350 Angstrom units that is greater than 0.50 cm³/g, and wherein the volume of pores with diameters in the range of 60–350 Angstrom units is greater than about 70% of the total contained pore volume; and
   c) contacting said catalyst with said hydrocarbon under conditions effective to cause dehydrogenation of said hydrocarbon to produce an olefin.

2. A process according to claim 1 in which the hydrocarbon is a paraffin.

3. A process according to claim 2 in which the paraffin is straight chain or branched, and is a detergent-range paraffin.

4. A process according to claim 1 in which the hydrocarbon comprises at least one unsaturated hydrocarbon.

5. A process according to claim 4 in which the hydrocarbon comprises a mixture of hydrocarbons wherein unsaturated hydrocarbons are present in an amount of less than 25.00% on a mass basis based upon the total mass of the hydrocarbon.

6. A process according to claim 1 in which the hydrocarbon comprises a mixture of hydrocarbons wherein unsaturated hydrocarbons comprise at least 25.00% of the mixture on a mass basis based upon the total mass of the hydrocarbon.

7. A process according to claim 1 in which the hydrocarbon comprises a mixture of hydrocarbons in which unsaturated hydrocarbons comprise at least 50.00% of the mixture on a mass basis based upon the total mass of the hydrocarbon.

8. A process according to claim 1 wherein said hydrocarbon comprises a straight chain detergent range paraffin.

9. A process according to claim 1 in which said catalyst is disposed within a reactor wherein the reactor includes:
   a) an inlet portion to which a raw material stream comprising a gaseous hydrocarbon is fed;
   b) a means for maintaining the catalyst in a substantially stationary position; and
   c) an outlet portion where effluent gases comprising at least one olefin exit said reactor.

10. A process according to claim 9 in which the hydrocarbon comprises at least one paraffin.

11. A process according to claim 10 in which the paraffin is straight chain or branched, and is a detergent-range paraffin.

12. A process according to claim 9 in which the hydrocarbon comprises an unsaturated hydrocarbon.

13. A process according to claim 9 in which the hydrocarbon comprises a saturated hydrocarbon.

14. A process according to claim 12 in which the hydrocarbon comprises a mixture of hydrocarbons wherein said unsaturated hydrocarbon is present in an amount of less than 25.00% on a mass basis based upon the total mass of the hydrocarbon.

15. A process according to claim 9 in which the hydrocarbon comprises a mixture of hydrocarbons wherein unsaturated hydrocarbons comprise at least 25.00% of the mixture on a mass basis based upon the total mass of the hydrocarbon.

16. A process according to claim 9 wherein said hydrocarbon comprises a straight chain detergent range paraffin.

17. A process according to claim 9 further comprising the step of:
   d) recovering a paraffin from said effluent gases.

18. A process according to claim 9 further comprising the step of:
   d) recovering a monoolefin from said effluent gases.

19. A process according to claim 9 further comprising the steps of:
   d) recovering a monoolefin from said effluent gases to provide a stripped effluent stream that contains a lower percentage of monoolefins than said effluent gases; and
   e) re-directing said stripped effluent stream to said inlet portion.

20. A process as in claim 19 further comprising the step of adding a gaseous hydrocarbon to the stripped effluent stream prior to the step of re-directing said stripped effluent stream to said inlet portion.

21. A process according to claim 9 wherein said raw material stream includes hydrogen in an effective amount for maintaining said catalyst in an active state.

22. A process according to claim 21 wherein the hydrogen to hydrocarbon mole ratio is within the range of 0.3 to 1.9.

23. A process according to claim 9 wherein the hydrocarbon is a paraffin and further comprising the steps of:
   d) recovering unreacted paraffins from said effluent; and
   e) re-directing said unreacted paraffins to said inlet portion of said reactor.

24. A process according to claim 10 further comprising the steps of:
   d) recovering unreacted paraffins from said effluent;
   e) mixing fresh paraffins with said unreacted paraffins to form a mixture; and
   f) feeding said mixture to said inlet portion.

25. A process according to claim 1 further comprising the step of: regenerating said catalyst.

26. A process according to claim 9 further comprising the step of: regenerating said catalyst.

27. A process according to claim 25 wherein regenerating said catalyst includes heating the catalyst in an oxygen-bearing atmosphere to a temperature sufficient to cause at least a portion of any coke present on the surface of said catalyst to be oxidized.

28. A process according to claim 26 wherein regenerating said catalyst includes heating the catalyst in an oxygen-bearing atmosphere to a temperature sufficient to cause at least a portion of any coke present on the surface of said catalyst to be oxidized.

29. A process for forming an olefin by dehydrogenation of a hydrocarbon which comprises the steps of:
   a) providing a hydrocarbon;
   b) providing a catalyst comprising:
      i) a primary catalytic component that comprises one or more elements selected from the group consisting of: platinum, rhodium, iridium, palladium, ruthenium, and osmium deposited on a porous alumina catalyst support, and
      ii) an acidity control component comprising at least one element selected from the group consisting of the alkali metals and the alkaline earth metals deposited upon said support,
   wherein said catalyst has a surface area greater than 100 m$^2$/g, a volume of pores with diameters below 60 Angstrom units that is less than 0.05 cm$^3$/g, a volume of pores with diameters in the range of 60–350 Angstrom units that is greater than 0.50 cm$^3$/g, and wherein the volume of pores with diameters in the range of 60–350 Angstrom units is greater than about 70% of the total contained pore volume; and
   c) contacting said catalyst with said hydrocarbon under conditions effective to cause dehydrogenation of said hydrocarbon to produce an olefin.

30. A process according to claim 29 in which the hydrocarbon is a paraffin.

31. A process according to claim 30 in which the paraffin is straight chain or branched, and is a detergent-range paraffin.

32. A process according to claim 29 in which the hydrocarbon comprises at least one unsaturated hydrocarbon.

33. A process according to claim 32 in which the hydrocarbon comprises a mixture of hydrocarbons wherein unsaturated hydrocarbons are present in an amount of less than 25.00% on a mass basis based upon the total mass of the hydrocarbon.

34. A process according to claim 29 in which the hydrocarbon comprises a mixture of hydrocarbons wherein unsaturated hydrocarbons comprise at least 25.00% of the mixture on a mass basis based upon the total mass of the hydrocarbon.

35. A process according to claim 29 in which the hydrocarbon comprises a mixture of hydrocarbons in which unsaturated hydrocarbons comprise at least 50.00% of the mixture on a mass basis based upon the total mass of the hydrocarbon.

36. A process according to claim 29 wherein said hydrocarbon comprises a straight chain detergent range paraffin.

37. A process according to claim 29 in which said catalyst is disposed within a reactor wherein the reactor includes:
   a) an inlet portion to which a raw material stream comprising a gaseous hydrocarbon is fed;
   b) a means for maintaining the catalyst in a substantially stationary position; and
   c) an outlet portion where effluent gases comprising at least one olefin exit said reactor.

38. A process according to claim 37 in which the hydrocarbon comprises at least one paraffin.

39. A process according to claim 38 in which the paraffin is straight chain or branched, and is a detergent-range paraffin.

40. A process according to claim 37 in which the hydrocarbon comprises an unsaturated hydrocarbon.

41. A process according to claim 37 in which the hydrocarbon comprises a saturated hydrocarbon.

42. A process according to claim 40 in which the hydrocarbon comprises a mixture of hydrocarbons wherein said unsaturated hydrocarbon is present in an amount of less than 25.00% on a mass basis based upon the total mass of the hydrocarbon.

43. A process according to claim 37 in which the hydrocarbon comprises a mixture of hydrocarbons wherein unsaturated hydrocarbons comprise at least 25.00% of the mixture on a mass basis based upon the total mass of the hydrocarbon.

44. A process according to claim 37 wherein said hydrocarbon comprises a straight chain detergent range paraffin.

45. A process according to claim 37 further comprising the step of:
   d) recovering a paraffin from said effluent gases.

46. A process according to claim 37 further comprising the step of:
   d) recovering a monoolefin from said effluent gases.

47. A process according to claim 37 further comprising the steps of:
   d) recovering a monoolefin from said effluent gases to provide a stripped effluent stream that contains a lower percentage of monoolefins than said effluent gases; and
   e) re-directing said stripped effluent stream to said inlet portion.

48. A process as in claim 47 further comprising the step of adding a gaseous hydrocarbon to the stripped effluent stream prior to the step of re-directing said stripped effluent stream to said inlet portion.

49. A process according to claim 37 wherein said raw material stream includes hydrogen in an effective amount for maintaining said catalyst in an active state.

50. A process according to claim 49 wherein the hydrogen to hydrocarbon mole ratio is within the range of 0.3 to 1.9.

51. A process according to claim 37 wherein the hydrocarbon is a paraffin and further comprising the steps of:
   d) recovering unreacted paraffins from said effluent; and
   e) re-directing said unreacted paraffins to said inlet portion of said reactor.

52. A process according to claim 38 further comprising the steps of:
   d) recovering unreacted paraffins from said effluent;

e) mixing fresh paraffins with said unreacted paraffins to form a mixture; and f) feeding said mixture to said inlet portion.

53. A process according to claim 29 further comprising the step of: regenerating said catalyst.

54. A process according to claim 37 further comprising the step of: regenerating said catalyst.

55. A process according to claim 53 wherein regenerating said catalyst includes heating the catalyst in an oxygen-bearing atmosphere to a temperature sufficient to cause at least a portion of any coke present on the surface of said catalyst to be oxidized.

56. A process according to claim 54 wherein regenerating said catalyst includes heating the catalyst in an oxygen-bearing atmosphere to a temperature sufficient to cause at least a portion of any coke present on the surface of said catalyst to be oxidized.

57. A process for forming an olefin by dehydrogenation of a hydrocarbon which comprises the steps of:

a) providing a hydrocarbon;

b) providing a catalyst comprising:
   i) a primary catalytic component that comprises one or more elements selected from the group consisting of: platinum, rhodium, iridium, palladium, ruthenium, and osmium deposited on a porous alumina catalyst support, and
   ii) an activator component comprising one or more elements selected from the group consisting of: scandium, titanium, vanadium, chromium, manganese, iron, cobalt, nickel, copper, zinc, yttrium, zirconium, niobium, molybdenum, silver, lanthanum, hafnium, tantalum, tungsten, rhenium, and gold deposited upon said support, wherein said catalyst has a surface area greater than 100 $m^2/g$, a volume of pores with diameters below 60 Angstrom units that is less than 0.05 $cm^3/g$, a volume of pores with diameters in the range of 60–350 Angstrom units that is greater than 0.50 $cm^3/g$, and wherein the volume of pores with diameters in the range of 60–350 Angstrom units is greater than about 70% of the total contained pore volume; and c) contacting said catalyst with said hydrocarbon under conditions effective to cause dehydrogenation of said hydrocarbon to produce an olefin.

58. A process according to claim 57 in which the hydrocarbon is a paraffin.

59. A process according to claim 58 in which the paraffin is straight chain or branched, and is a detergent-range paraffin.

60. A process according to claim 57 in which the hydrocarbon comprises at least one unsaturated hydrocarbon.

61. A process according to claim 60 in which the hydrocarbon comprises a mixture of hydrocarbons wherein unsaturated hydrocarbons are present in an amount of less than 25.00% on a mass basis based upon the total mass of the hydrocarbon.

62. A process according to claim 57 in which the hydrocarbon comprises a mixture of hydrocarbons wherein unsaturated hydrocarbons comprise at least 25.00% of the mixture on a mass basis based upon the total mass of the hydrocarbon.

63. A process according to claim 57 in which the hydrocarbon comprises a mixture of hydrocarbons in which unsaturated hydrocarbons comprise at least 50.00% of the mixture on a mass basis based upon the total mass of the hydrocarbon.

64. A process according to claim 57 wherein said hydrocarbon comprises a straight chain detergent range paraffin.

65. A process according to claim 57 in which said catalyst is disposed within a reactor wherein the reactor includes:

a) an inlet portion to which a raw material stream comprising a gaseous hydrocarbon is fed;

b) a means for maintaining the catalyst in a substantially stationary position; and c) an outlet portion where effluent gases comprising at least one olefin exit said reactor.

66. A process according to claim 65 in which the hydrocarbon comprises at least one paraffin.

67. A process according to claim 66 in which the paraffin is straight chain or branched, and is a detergent-range paraffin.

68. A process according to claim 65 in which the hydrocarbon comprises an unsaturated hydrocarbon.

69. A process according to claim 65 in which the hydrocarbon comprises a saturated hydrocarbon.

70. A process according to claim 68 in which the hydrocarbon comprises a mixture of hydrocarbons wherein said unsaturated hydrocarbon is present in an amount of less than 25.00% on a mass basis based upon the total mass of the hydrocarbon.

71. A process according to claim 65 in which the hydrocarbon comprises a mixture of hydrocarbons wherein unsaturated hydrocarbons comprise at least 25.00% of the mixture on a mass basis based upon the total mass of the hydrocarbon.

72. A process according to claim 65 wherein said hydrocarbon comprises a straight chain detergent range paraffin.

73. A process according to claim 65 further comprising the step of:

d) recovering a paraffin from said effluent gases.

74. A process according to claim 65 further comprising the step of:

d) recovering a monoolefin from said effluent gases.

75. A process according to claim 65 further comprising the steps of:

d) recovering a monoolefin from said effluent gases to provide a stripped effluent stream that contains a lower percentage of monoolefins than said effluent gases; and e) re-directing said stripped effluent stream to said inlet portion.

76. A process as in claim 75 further comprising the step of adding a gaseous hydrocarbon to the stripped effluent stream prior to the step of re-directing said stripped effluent stream to said inlet portion.

77. A process according to claim 65 wherein said raw material stream includes hydrogen in an effective amount for maintaining said catalyst in an active state.

78. A process according to claim 77 wherein the hydrogen to hydrocarbon mole ratio is within the range of 0.3 to 1.9.

79. A process according to claim 65 wherein the hydrocarbon is a paraffin and further comprising the steps of:

d) recovering unreacted paraffins from said effluent; and e) re-directing said unreacted paraffins to said inlet portion of said reactor.

80. A process according to claim 66 further comprising the steps of:

d) recovering unreacted paraffins from said effluent;

e) mixing fresh paraffins with said unreacted paraffins to form a mixture; and f) feeding said mixture to said inlet portion.

81. A process according to claim 57 further comprising the step of regenerating said catalyst.

82. A process according to claim 65 further comprising the step of: regenerating said catalyst.

83. A process according to claim 81 wherein regenerating said catalyst includes heating the catalyst in an oxygen-bearing atmosphere to a temperature sufficient to cause at least a portion of any coke present on the surface of said catalyst to be oxidized.

84. A process according to claim 82 wherein regenerating said catalyst includes heating the catalyst in an oxygen-bearing atmosphere to a temperature sufficient to cause at least a portion of any coke present on the surface of said catalyst to be oxidized.

85. A process for forming an olefin by dehydrogenation of a hydrocarbon which comprises the steps of:
 a) providing a hydrocarbon;
 b) providing a catalyst comprising:
  i) a primary catalytic component that comprises one or more elements selected from the group consisting of: platinum, rhodium, iridium, palladium, ruthenium, and osmium deposited on a porous alumina catalyst support;
  ii) an activator component comprising one or more elements selected from the group consisting of: scandium, titanium, vanadium, chromium, manganese, iron, cobalt, nickel, copper, zinc, yttrium, zirconium, niobium, molybdenum, silver, lanthanum, hafnium, tantalum, tungsten, rhenium, and gold deposited upon said support; and
  iii) an acidity control component comprising at least one element selected from the group consisting of the alkali metals and the alkaline earth metals deposited upon said support,
 wherein said catalyst has a surface area greater than 100 $m^2/g$, a volume of pores with diameters below 60 Angstrom units that is less than 0.05 $cm^3/g$, a volume of pores with diameters in the range of 60–350 Angstrom units that is greater than 0.50 $cm^3/g$, and wherein the volume of pores with diameters in the range of 60–350 Angstrom units is greater than about 70% of the total contained pore volume; and
 c) contacting said catalyst with said hydrocarbon under conditions effective to cause dehydrogenation of said hydrocarbon to produce an olefin.

86. A process according to claim 85 in which the hydrocarbon is a paraffin.

87. A process according to claim 86 in which the paraffin is straight chain or branched, and is a detergent-range paraffin.

88. A process according to claim 85 in which the hydrocarbon comprises at least one unsaturated hydrocarbon.

89. A process according to claim 88 in which the hydrocarbon comprises a mixture of hydrocarbons wherein unsaturated hydrocarbons are present in an amount of less than 25.00% on a mass basis based upon the total mass of the hydrocarbon.

90. A process according to claim 85 in which the hydrocarbon comprises a mixture of hydrocarbons wherein unsaturated hydrocarbons comprise at least 25.00% of the mixture on a mass basis based upon the total mass of the hydrocarbon.

91. A process according to claim 85 in which the hydrocarbon comprises a mixture of hydrocarbons in which unsaturated hydrocarbons comprise at least 50.00% of the mixture on a mass basis based upon the total mass of the hydrocarbon.

92. A process according to claim 85 wherein said hydrocarbon comprises a straight chain detergent range paraffin.

93. A process according to claim 85 in which said catalyst is disposed within a reactor wherein the reactor includes:
 a) an inlet portion to which a raw material stream comprising a gaseous hydrocarbon is fed;
 b) a means for maintaining the catalyst in a substantially stationary position; and
 c) an outlet portion where effluent gases comprising at least one olefin exit said reactor.

94. A process according to claim 93 in which the hydrocarbon comprises at least one paraffin.

95. A process according to claim 94 in which the paraffin is straight chain or branched, and is a detergent-range paraffin.

96. A process according to claim 93 in which the hydrocarbon comprises an unsaturated hydrocarbon.

97. A process according to claim 93 in which the hydrocarbon comprises a saturated hydrocarbon.

98. A process according to claim 96 in which the hydrocarbon comprises a mixture of hydrocarbons wherein said unsaturated hydrocarbon is present in an amount of less than 25.00% on a mass basis based upon the total mass of the hydrocarbon.

99. A process according to claim 93 in which the hydrocarbon comprises a mixture of hydrocarbons wherein unsaturated hydrocarbons comprise at least 25.00% of the mixture on a mass basis based upon the total mass of the hydrocarbon.

100. A process according to claim 93 wherein said hydrocarbon comprises a straight chain detergent range paraffin.

101. A process according to claim 93 further comprising the step of:
 d) recovering a paraffin from said effluent gases.

102. A process according to claim 93 further comprising the step of:
 d) recovering a monoolefin from said effluent gases.

103. A process according to claim 93 further comprising the steps of:
 d) recovering a monoolefin from said effluent gases to provide a stripped effluent stream that contains a lower percentage of monoolefins than said effluent gases; and
 e) re-directing said stripped effluent stream to said inlet portion.

104. A process as in claim 103 further comprising the step of adding a gaseous hydrocarbon to the stripped effluent stream prior to the step of re-directing said stripped effluent stream to said inlet portion.

105. A process according to claim 93 wherein said raw material stream includes hydrogen in an effective amount for maintaining said catalyst in an active state.

106. A process according to claim 105 wherein the hydrogen to hydrocarbon mole ratio is within the range of 0.3 to 1.9.

107. A process according to claim 93 wherein the hydrocarbon is a paraffin and further comprising the steps of:
 d) recovering unreacted paraffins from said effluent; and
 e) re-directing said unreacted paraffins to said inlet portion of said reactor.

108. A process according to claim 94 further comprising the steps of:
 d) recovering unreacted paraffins from said effluent;
 e) mixing fresh paraffins with said unreacted paraffins to form a mixture; and
 f) feeding said mixture to said inlet portion.

109. A process according to claim 85 further comprising the step of: regenerating said catalyst.

110. A process according to claim 93 further comprising the step of: regenerating said catalyst.

111. A process according to claim 109 wherein regenerating said catalyst includes heating the catalyst in an oxygen-bearing atmosphere to a temperature sufficient to cause at least a portion of any coke present on the surface of said catalyst to be oxidized.

112. A process according to claim 110 wherein regenerating said catalyst includes heating the catalyst in an oxygen-bearing atmosphere to a temperature sufficient to cause at least a portion of any coke present on the surface of said catalyst to be oxidized.

113. A process for forming an olefin by dehydrogenation of a hydrocarbon which comprises the steps of:
  a) providing a hydrocarbon;
  b) providing a catalyst comprising:
    i) a primary catalytic component that comprises platinum deposited on a porous alumina catalyst support;
    ii) an activator component comprising one or more elements selected from the group consisting of: copper, silver, and gold present in an amount between 0.10% and 5.00% by weight based on the total weight of the and catalyst, including every hundredth percentage therebetween, deposited upon said support; and
    iii) an acidity control component comprising at least one element selected from the group consisting of the alkali metals and the alkaline earth metals present in an amount between 0.001% and 1.000% by weight based on the total weight of the catalyst, including every thousandth percentage therebetween, deposited upon said support,
  wherein said catalyst has a surface area greater than 100 $m^2/g$, a volume of pores with diameters below 60 Angstrom units that is less than 0.05 $cm^3/g$, a volume of pores with diameters in the range of 60–350 Angstrom units that is greater than 0.50 $cm^3/g$, and wherein the volume of pores with diameters in the range of 60–350 Angstrom units is greater than about 70% of the total contained pore volume; and
  c) contacting said catalyst with said hydrocarbon under conditions effective to cause dehydrogenation of said hydrocarbon to produce an olefin.

114. A process according to claim 113 in which the hydrocarbon is a paraffin.

115. A process according to claim 114 in which the paraffin is straight chain or branched, and is a detergent-range paraffin.

116. A process according to claim 113 in which the hydrocarbon comprises at least one unsaturated hydrocarbon.

117. A process according to claim 116 in which the hydrocarbon comprises a mixture of hydrocarbons wherein unsaturated hydrocarbons are present in an amount of less than 25.00% on a mass basis based upon the total mass of the hydrocarbon.

118. A process according to claim 113 in which the hydrocarbon comprises a mixture of hydrocarbons wherein unsaturated hydrocarbons comprise at least 25.00% of the mixture on a mass basis based upon the total mass of the hydrocarbon.

119. A process according to claim 113 in which the hydrocarbon comprises a mixture of hydrocarbons in which unsaturated hydrocarbons comprise at least 50.00% of the mixture on a mass basis based upon the total mass of the hydrocarbon.

120. A process according to claim 113 wherein said hydrocarbon comprises a straight chain detergent range paraffin.

121. A process according to claim 113 in which said catalyst is disposed within a reactor wherein the reactor includes:
  a) an inlet portion to which a raw material stream comprising a gaseous hydrocarbon is fed;
  b) a means for maintaining the catalyst in a substantially stationary position; and
  c) an outlet portion where effluent gases comprising at least one olefin exit said reactor.

122. A process according to claim 121 in which the hydrocarbon comprises at least one paraffin.

123. A process according to claim 122 in which the paraffin is straight chain or branched, and is a detergent-range paraffin.

124. A process according to claim 121 in which the hydrocarbon comprises an unsaturated hydrocarbon.

125. A process according to claim 121 in which the hydrocarbon comprises a saturated hydrocarbon.

126. A process according to claim 124 in which the hydrocarbon comprises a mixture of hydrocarbons wherein said unsaturated hydrocarbon is present in an amount of less than 25.00% on a mass basis based upon the total mass of the hydrocarbon.

127. A process according to claim 121 in which the hydrocarbon comprises a mixture of hydrocarbons wherein unsaturated hydrocarbons comprise at least 25.00% of the mixture on a mass basis based upon the total mass of the hydrocarbon.

128. A process according to claim 121 wherein said hydrocarbon comprises a straight chain detergent range paraffin.

129. A process according to claim 121 further comprising the step of:
  d) recovering a paraffin from said effluent gases.

130. A process according to claim 121 further comprising the step of:
  d) recovering a monoolefin from said effluent gases.

131. A process according to claim 121 further comprising the steps of:
  d) recovering a monoolefin from said effluent gases to provide a stripped effluent stream that contains a lower percentage of monoolefins than said effluent gases; and
  e) re-directing said stripped effluent stream to said inlet portion.

132. A process as in claim 131 further comprising the step of adding a gaseous hydrocarbon to the stripped effluent stream prior to the step of re-directing said stripped effluent stream to said inlet portion.

133. A process according to claim 121 wherein said raw material stream includes hydrogen in an effective amount for maintaining said catalyst in an active state.

134. A process according to claim 133 wherein the hydrogen to hydrocarbon mole ratio is within the range of 0.3 to 1.9.

135. A process according to claim 121 wherein the hydrocarbon is a paraffin and further comprising the steps of:
  d) recovering unreacted paraffins from said effluent; and e) re-directing said unreacted paraffins to said inlet portion of said reactor.

136. A process according to claim 122 further comprising the steps of:
d) recovering unreacted paraffins from said effluent;
e) mixing fresh paraffins with said unreacted paraffins to form a mixture; and
f) feeding said mixture to said inlet portion.

137. A process according to claim 113 further comprising the step of: regenerating said catalyst.

138. A process according to claim 121 further comprising the step of: regenerating said catalyst.

139. A process according to claim 137 wherein regenerating said catalyst includes heating the catalyst in an oxygen-bearing atmosphere to a temperature sufficient to cause at least a portion of any coke present on the surface of said catalyst to be oxidized.

140. A process according to claim 138 wherein regenerating said catalyst includes heating the catalyst in an oxygen-bearing atmosphere to a temperature sufficient to cause at least a portion of any coke present on the surface of said catalyst to be oxidized.

* * * * *